United States Patent
Akl et al.

(10) Patent No.: US 10,470,716 B2
(45) Date of Patent: Nov. 12, 2019

(54) SIGNAL ANALYZER SYSTEM FOR MONITORING BIO-MEDIA, ANALYSIS OF MOTION-INDUCED SIGNAL MODULATION

(71) Applicant: Analog Devices, Inc., Norwood, MA (US)

(72) Inventors: Tony J. Akl, Woburn, MA (US); James C. Doscher, Reading, MA (US)

( * ) Notice: Subject to any disclaimer, the term of this patent is extended or adjusted under 35 U.S.C. 154(b) by 490 days.

(21) Appl. No.: 15/229,494

(22) Filed: Aug. 5, 2016

(65) Prior Publication Data

US 2018/0035950 A1 Feb. 8, 2018

(51) Int. Cl.
*A61B 5/1455* (2006.01)
*A61B 5/00* (2006.01)
*G01N 33/49* (2006.01)
*A61B 5/02* (2006.01)

(52) U.S. Cl.
CPC .......... *A61B 5/721* (2013.01); *A61B 5/14552* (2013.01); *A61B 5/7207* (2013.01); *G01N 33/4925* (2013.01); *A61B 5/02007* (2013.01); *A61B 5/725* (2013.01)

(58) Field of Classification Search
CPC ... A61B 5/0205; A61B 5/0059; A61B 5/1455; A61B 5/14551; A61B 5/14552; A61B 5/721; A61B 5/725; A61B 5/7207; A61B 5/02007
See application file for complete search history.

(56) References Cited

U.S. PATENT DOCUMENTS

| 4,854,699 | A | | 8/1989 | Edgar, Jr. | |
|---|---|---|---|---|---|
| 5,431,170 | A | * | 7/1995 | Mathews | A61B 5/0002 600/323 |
| 6,018,673 | A | * | 1/2000 | Chin | A61B 5/14552 356/41 |
| 6,334,065 | B1 | * | 12/2001 | Al-Ali | A61B 5/14551 600/323 |

(Continued)

FOREIGN PATENT DOCUMENTS

WO  2016/014833  1/2016

OTHER PUBLICATIONS

International Search Report and Written Opinion issued in International Patent Application Serial No. PCT/US2017/045798 dated Nov. 19, 2017, 21 pages.

*Primary Examiner* — Eric F Winakur
*Assistant Examiner* — Chu Chuan Liu
(74) *Attorney, Agent, or Firm* — Patent Capital Group

(57) ABSTRACT

According to one configuration, a system includes sensor hardware and signal processor resource to monitor and analyze bio-media (such as blood and/or other matter) of a person under test. During operation, the sensor hardware monitors the bio-media of the person under test and produces an output. The monitored output (such as one or more signals) varies in magnitude based at least in part on person-induced movement. The signal processor resource analyzes the output produced by the sensor hardware. Based on the analysis, and detected variation in the output of the (Continued)

sensor hardware as caused by the person's movement, the signal processor resource produces a setting for a biometric parameter of interest associated with monitoring the biomedia. Note that the system as described herein can be used to measure different biometric parameters of interest such as venous blood oxygen content, vein stiffness, etc.

20 Claims, 15 Drawing Sheets

(56) References Cited

U.S. PATENT DOCUMENTS

| | | |
|---|---|---|
| 6,947,781 B2 | 9/2005 | Asada et al. |
| 7,263,395 B2 | 8/2007 | Chan et al. |
| 8,229,530 B2 | 7/2012 | Baker, Jr. et al. |
| 8,271,063 B2 | 9/2012 | Dietiker |
| 8,321,003 B2 | 11/2012 | Zhang et al. |
| 8,417,305 B2 | 4/2013 | Dixon |
| 8,954,135 B2 | 2/2015 | Yuen et al. |
| 2009/0259116 A1* | 10/2009 | Wasserman ........ A61B 5/14551 600/323 |
| 2012/0277561 A1 | 11/2012 | Baker, Jr. et al. |
| 2013/0258086 A1 | 10/2013 | Erhart et al. |
| 2015/0208965 A1 | 7/2015 | Watson et al. |

* cited by examiner

SIGNAL ANALYZER SYSTEM FOR MONITORING BIO-MEDIA, ANALYSIS OF MOTION-INDUCED SIGNAL MODULATION

FIELD OF THE DISCLOSURE

The present disclosure is generally directed to apparatus, methods, computer-readable media, etc., operable to analyze bio-media of a person under test to determine a setting for respective one or more biometric parameters of interest. In a specific non-limiting example embodiment, as further described herein, the bio-media analyzed is venous blood and the biometric parameter is a level of oxygen content.

BACKGROUND

Oxygen saturation (symbol $SO_2$) is a relative measure of the amount of oxygen that is dissolved or carried in a given medium such as blood. Oxygen saturation is typically measured in percent (%) and is useful to monitor a respective subjects overall oxygen supply and consumption.

Oxygen saturation of blood in a subject can be measured in a number of different ways. For example, conventional techniques include both invasive and noninvasive methods to determine oxygen saturation in blood.

According to conventional invasive techniques, a catheter including an oxygen sensor is inserted (in a subcutaneous manner) into a blood vessel of the respective subject. The oxygen sensor in the catheter in contact with blood generates respective one or more signals. An analyzer analyzes the signals to measure an amount of oxygen in the blood.

Arterial oxygen saturation (SaO2) is commonly measured using so-called pulse oximetry techniques. According to this non-invasive technique, a selected site of the patient under test is exposed to an optical signal. A photo detector detects an intensity of the optical signal transmitted through or reflected off the high-pressure, pulsing blood at the selected site. An analyzer determines an AC component of the absorbance at each wavelength and then divides it by the corresponding DC component to obtain a ratio that is independent of the incident light intensity. The analyzer uses a ratio of the ratios on different wavelengths to determine oxygen content in the artery (media having a pulse). This technique provides the oxygen saturation in the artery (or the capillaries). The signal obtained from pulse oximetry can also be used to measure other parameters of the arterial and capillary networks such as vessel stiffness.

SUMMARY OF THE DISCLOSURE

This disclosure includes the observation that since venous blood normally does not pulsate, the AC component as discussed above cannot be obtained for venous blood. Accordingly, conventional pulse oximetry cannot be used to measure venous blood oxygenation levels.

In contrast to conventional techniques, embodiments herein include a system to measure and monitor one or more biometric parameters (such as blood oxygen content, vein stiffness, etc.) of a subject such as a person, animal, etc., based at least in part motion-induced signal variations. An example apparatus comprises: sensor hardware and signal processor resource. During operation, the sensor hardware monitors bio-media (such as blood) of the subject under test (such as a person) and produces an output (such as one or more signals) indicative of oxygen levels in the monitored bio-media. The monitored output varies in magnitude based at least in part on movement of a body part of the subject under test. The signal processor resource analyzes the output from the sensor hardware. Based on the analysis, the signal processor resource produces setting information for one or more biometric parameters associated with the bio-media using the detected variation(s) in the output of the sensor hardware as caused by the subject's body movement.

Thus, the present disclosure is generally directed to apparatus, methods, computer-readable media, etc., operable to detect and analyze motion-induced variations (modulation) in monitored bio-media such as blood or other suitable matter.

In one embodiment, the sensor hardware is secured to a body part of the subject under test. The subject under test voluntarily controls the movement of the body part of the subject under test (such as in accordance with instructions provided to the subject under test) to apply forces to the bio-media under test, causing the variation in the output from the sensor hardware. Accordingly, in one embodiment, subject-induced motion of a body part of the subject under test (such as a patient, athlete, etc.) causes a variation in the output generated by the sensor hardware. The signal processor resource uses the motion-induced signal variations (modulation) to determine a setting for the monitored biometric parameter such as a level of oxygen in the venous blood of the subject under test, vein stiffness, etc.

In accordance with further embodiments, the output from the sensor hardware represents a reflected portion of an optical signal directed at a site on the subject under test monitored as detected by the sensor hardware. Additionally or alternatively, the output represents a portion of an optical signal passing through (transmissive) the subject under test.

In accordance with still further embodiments, the motion of the subject under test can be inferred from variations in the output generated by the sensor hardware.

As an alternative to inferring motion, the analyzer apparatus as described herein can receive further input indicating an amount and/or type associated with the movement. For example, the system as described herein can further include a motion sensor that produces a motion signal measuring the movement of the subject under test. The signal processor resource uses the motion signal as a basis to identify one or more attributes (such as timing, frequency, period, direction, magnitude, etc.) associated with the movement of the subject under test. Any of one or more of such parameters can be used to facilitate measuring of the variation in the output signal caused by the subject's movement.

In furtherance of producing the setting for a biometric parameter of interest, the signal processor resource can be configured to: identify a frequency range associated with the movement of the subject under test; produce a filter to pass portions of the output signal in the frequency range; and pass the output signal through the filter to measure the variation in the output caused by the movement. In such an embodiment, the signal processor resource produces the setting for the biometric parameter of interest based at least in part on the variation in the output of the sensor hardware as detected in the frequency range.

In yet further embodiments, the signal processor resource is operable to produce the setting for the biometric parameter of interest (of the monitored bio-media) based at least in part on a ratio of a magnitude of the variation in the output to an average magnitude of the output. More specifically, the output from respective monitoring hardware can include a first output signal and second output signal. The first output signal varies in magnitude based on the movement of the subject under test; the second output signal varies in magnitude based on the movement of the subject under test. In such an embodiment, the signal processor resource produces a first ratio value and a secondary circuit ratio value. The first ratio value represents a ratio of the magnitude of the variation in the first output signal to an average magnitude of the first output signal; the second ratio value represents a ratio of the magnitude of the variation in the second output signal to an average magnitude of the second output signal. Further, the signal processor resource produces the setting for the biometric parameter of interest based at least in part on dividing the first ratio value by the second ratio value.

These and other more specific embodiments are disclosed in more detail below.

Note that any of the resources as discussed herein can include one or more computerized devices, medical devices, mobile devices, servers, base stations, wireless playback equipment, handheld or laptop computers, or the like to carry out and/or support any or all of the method operations disclosed herein. In other words, one or more computerized devices or processors can be programmed and/or configured to operate as explained herein to carry out the different embodiments as described herein.

Yet other embodiments herein include software programs to perform the steps and operations summarized above and disclosed in detail below. One such embodiment comprises a computer program product including a non-transitory computer-readable storage medium (i.e., any computer readable hardware storage medium or hardware storage media disparately or co-located) on which software instructions are encoded for subsequent execution. The instructions, when executed in a computerized device (hardware) having a processor, program and/or cause the processor (hardware) to perform any of the operations disclosed herein. Such arrangements are typically provided as software, code, instructions, and/or other data (e.g., data structures) arranged or encoded on a non-transitory computer readable storage media such as an optical medium (e.g., CD-ROM), floppy disk, hard disk, memory stick, memory device, etc., or other a medium such as firmware in one or more ROM, RAM, PROM, etc., and/or as an Application Specific Integrated Circuit (ASIC), etc. The software or firmware or other such configurations can be installed onto a computerized device to cause the computerized device to perform any operations explained herein.

Accordingly, embodiments herein are directed to methods, apparatus, computer program products, computer-readable media, etc., that support operations as discussed herein.

One embodiment includes a computer readable storage media and/or a apparatus having instructions stored thereon to facilitate monitoring of bio-media of a respective subject under test. For example, in one embodiment, the instructions, when executed by computer processor hardware, cause the computer processor hardware (such as one or more processor devices) to: monitor a subject under test; produce an output signal that varies in magnitude based on movement of the subject under test; and produce a setting for the biometric parameter based at least in part on detected variation in the output signal caused by the movement.

The ordering of the steps above has been added for clarity sake. Note that any of the processing steps as discussed herein can be performed in any suitable order.

Other embodiments of the present disclosure include software programs and/or respective hardware to perform any of the method embodiment steps and operations summarized above and disclosed in detail below.

It is to be understood that the apparatus, method, system, instructions on computer readable storage media, etc., as discussed herein also can be embodied strictly as a software program, firmware, as a hybrid of software, hardware and/or firmware, or as hardware alone such as within a processor (hardware or software), or within an operating apparatus or a within a software application.

As discussed herein, techniques herein are well suited for use in the field of bio-media monitoring applications. However, it should be noted that embodiments herein are not limited to use in such applications and that the techniques discussed herein are well suited for other applications as well.

Additionally, note that although each of the different features, techniques, configurations, etc., herein may be discussed in different places of this disclosure, it is intended, where suitable, that each of the concepts can optionally be executed independently of each other or in combination with each other. Accordingly, the one or more present inventions as described herein can be embodied and viewed in many different ways.

Also, note that this preliminary discussion of embodiments herein purposefully does not specify every embodiment and/or incrementally novel aspect of the present disclosure or claimed invention(s). Instead, this brief description only presents general embodiments and corresponding points of novelty over conventional techniques. For additional details and/or possible perspectives (permutations) of the invention(s), the reader is directed to the Detailed Description section and corresponding figures of the present disclosure as further discussed below.

Figure 1:
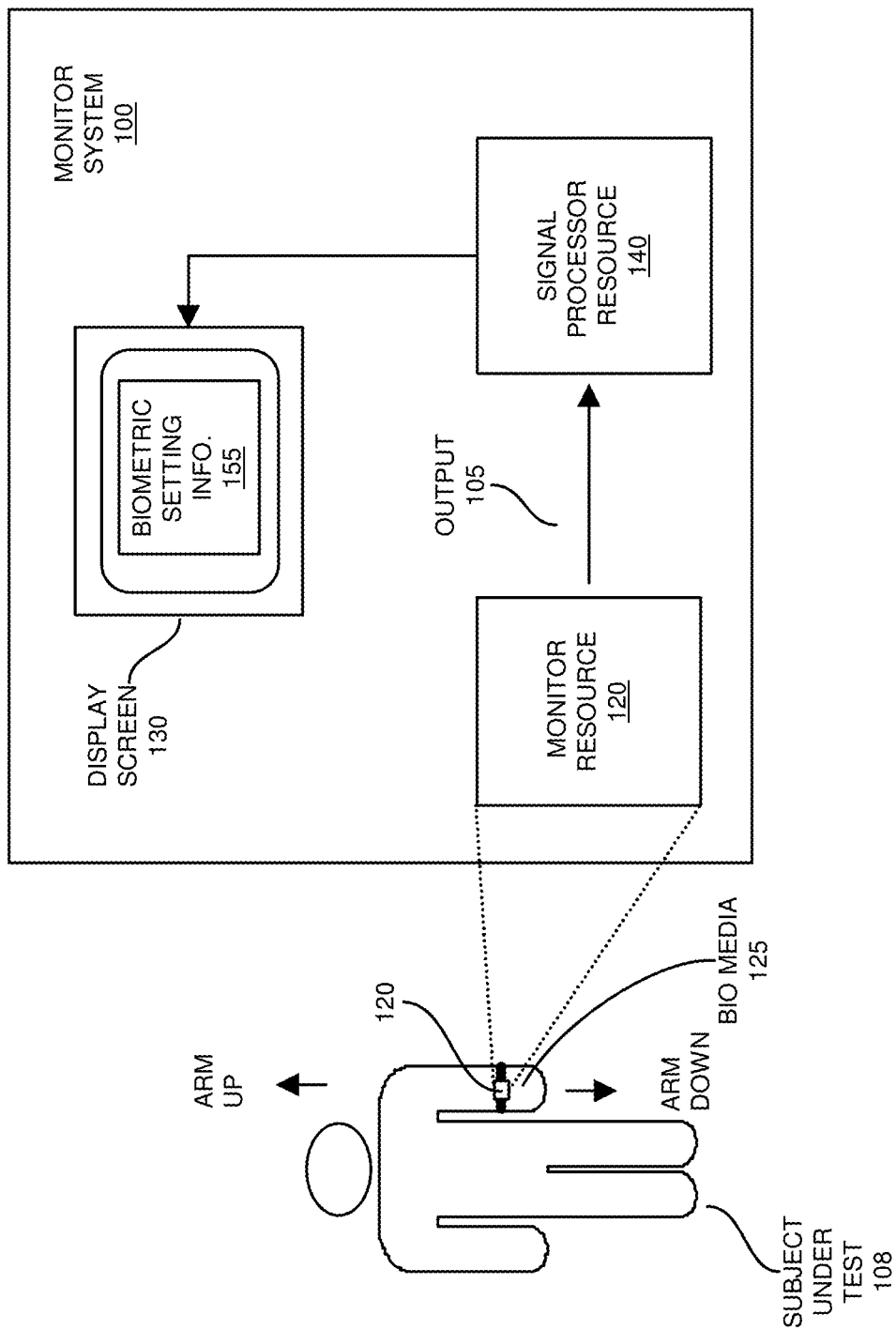
FIG. 1 is an example diagram illustrating a bio-media monitor system according to embodiments herein.

The foregoing and other objects, features, and advantages of the invention will be apparent from the following more particular description of preferred embodiments herein, as illustrated in the accompanying drawings in which like reference characters refer to the same parts throughout the different views. The drawings are not necessarily to scale, with emphasis instead being placed upon illustrating the embodiments, principles, concepts, etc.

DETAILED DESCRIPTION

The present disclosure includes the observation that conventional pulse oximetry techniques used to monitor arterial blood cannot be used to accurately measure oxygen content in venous blood because venous blood does not have a pulse as does arterial blood. Additionally, the present disclosure further includes the observation that voluntary or involuntary movement of a subject under test induces variations in (or modulation of) one or more signals outputted from sensor hardware monitoring a fluid medium such as blood of the subject under test. In one specific embodiment, as further discussed during, a signal processor resource uses the detected variations in the monitored one or more signals from respective sensor hardware to determine a setting of a biometric parameter such as oxygen content in venous blood of the subject under test.

Accordingly, embodiments herein include sensor hardware and signal processor resource to monitor and analyze bio-media (such as blood) of a subject under test. During operation, the sensor hardware monitors the bio-media of the subject under test and produces an output. The monitored output (such as one or more signals) varies in magnitude based at least in part on subject-induced movement. Signal processor resource analyzes the output produced by the sensor hardware. Based on the analysis, and detected variation in the output of the sensor hardware as caused by the subject's movement, the signal processor resource produces a setting for a biometric parameter of interest associated with monitoring of the bio-media.

Note that the system as described herein can be used to measure different biometric parameters of interest such as venous blood oxygen content, vein stiffness, etc.

Now, more specifically, and with reference to the figures, FIG. 1 is an example diagram illustrating a monitor system according to embodiments herein.

As shown, monitor system 100 includes monitor resource 120, signal processor resource 140, and display screen 130. Note that each of the components such as monitor resource 120, signal processor resource 140, etc., associated with monitor system 100 includes hardware and/or software to execute respective operations as discussed herein. Thus, monitor resource 120 can be a hardware resource and/or a software resource; signal processor resource 140 can be a hardware resource and/or a software resource; and so on.

In one embodiment, monitor resource 120 is affixed to a suitable body part such as an arm, a leg, etc., of the subject under test 108 (such as a person, patient, animal, etc.). During operation, the monitor resource 120 monitors bio-media 125 (such as any of one or more of the following matter including blood, tissue, bone, etc.) associated with the subject under test 108.

More specifically, in one embodiment, the monitor resource 120 affixed to the body part of the subject under test 108 produces output 105 as shown. The monitor resource (including corresponding sensor hardware) can be disposed on an external surface (such as skin) of the subject under test 108 to non-invasively monitor bio-media 125 such as venous blood flowing through the subject under test 108. As further discussed herein, a volume of the monitored bio-media 125 (such as low pressure, flowing venous blood) varies due to the motion of the subject under test 108.

The monitor resource 120 conveys the output 105 from the monitor resource 120 to the signal processor resource 140. Thus, the signal processor resource 140 receives the output 105 generated by the monitor resource 120.

Note that the signal processor resource 140 can be configured to receive the output 105 in any suitable manner. For example, in one embodiment, the monitor resource 120 affixed to the arm of the subject under test 108 (in this example) can include a wireless interface to communicate the output 105 over a wireless link to the signal processor resource 140. Alternatively, the monitor resource 120 can be configured to communicate the output 105 over a hardwired link (such as one or more cables, wires, etc.) connecting the monitor resource 120 to the signal processor resource 140.

In accordance with further embodiments, the monitor resource 120 is secured to an appendage (such as an arm) of the subject under test 108. The subject under test 108 moves his/her appendage up and down, side-to-side, etc., while the monitor resource 120 monitors respective bio-media 125 of the subject under test 108. Note that the self-induced motion can be repetitive or be a single non-repetitive motion such as standing up after sitting in a chair, raising an arm in the air, jumping, etc.

Note that attachment of the monitor resource 120 to the wrist or arm of the subject under test 108 is shown by way of non-limiting example only. That is, the monitor resource 120 can be affixed to any suitable body part or location of the subject under test 108.

The signal processor resource 140 receives the output 105 (such as one or more signals) generated by the monitor resource 120 during the monitoring of the respective bio-media 125. The magnitude of output 105 varies depending upon a degree of motion induced by the subject under test 108.

Note that the motion of the subject under test 108 need not be the appendage to which the monitor resource 120 is affixed. For example, in one embodiment, a subject under test 108 may place the monitor resource 120 to a left wrist; movement of another body part of the subject under test such as a right arm or right wrist may cause sufficient variation to the bio-media 125 to produce variations in output 105.

As further shown, the signal processor resource 140 receives the output 105 and analyzes it to produce biometric setting information 155 for display on a respective display screen 130. Biometric setting information 155 can include settings for one or more biometric parameters (such as venous blood oxygen content, vein stiffness, etc.).

As further discussed, the signal processor resource 140 produces settings for the one or more biometric parameters (being monitored) based at least in part on detected one or more variations in the output 105 caused by the movement of the subject under test 108.

Figure 2:
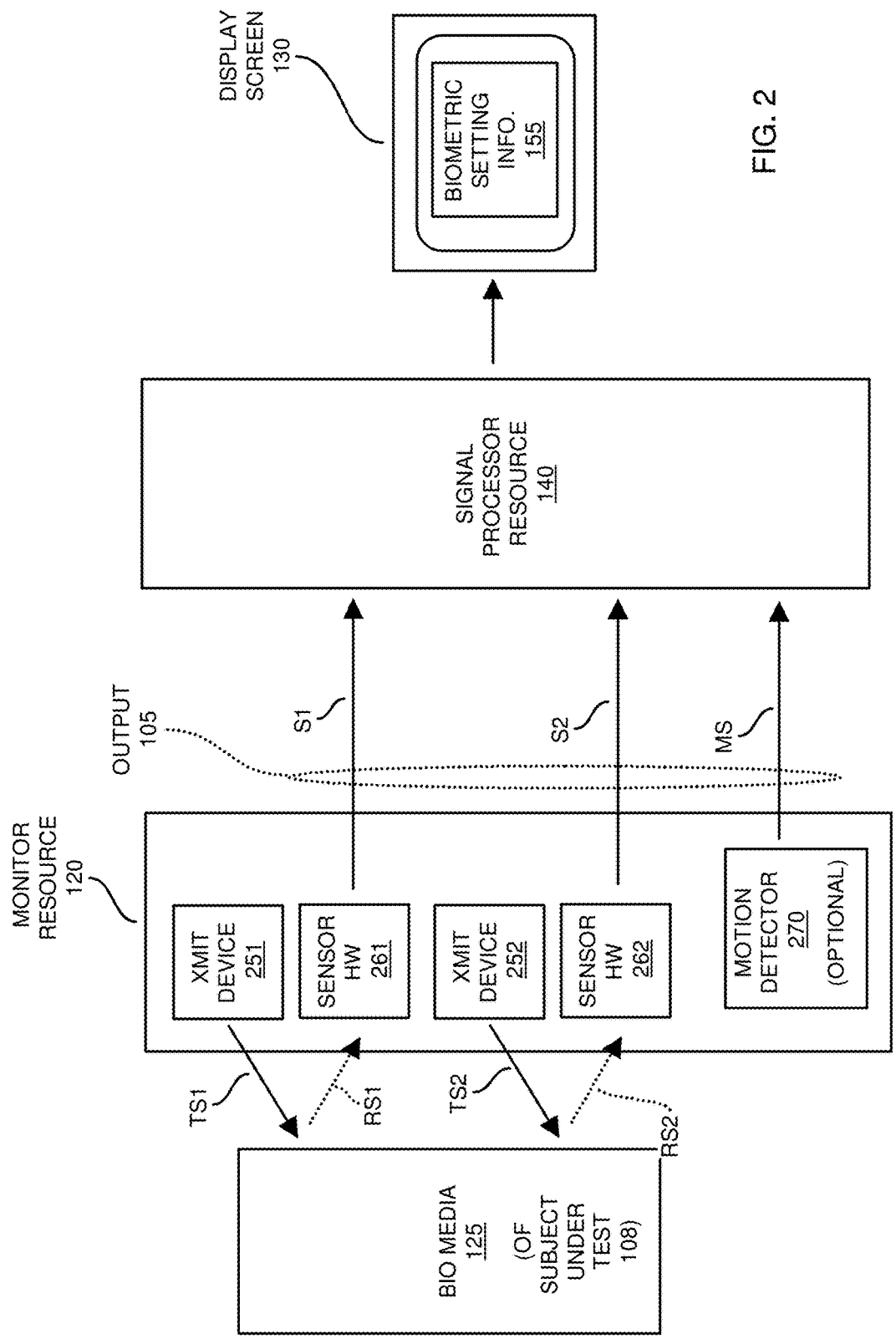
FIG. 2 is an example diagram illustrating use of monitor hardware to monitor bio-media, analysis of sensor-generated signals to produce display information, and display of corresponding monitor results according to embodiments herein.

FIG. 2 is an example diagram illustrating use of monitor resource to monitor bio-media, analysis of sensor-generated signals to produce display information, and display of corresponding biometric parameter results according to embodiments herein.

As further shown in this example embodiment, the monitor resource 120 includes transmitter device 251 and transmitter device 252.

By way of non-limiting example, the transmitter device 251 transmits optical signal TS1 (such as at a first optical wavelength) at or through bio-media 125. Bio-media 125 can include any of more of the following matter: blood, tissue, bone, cartilage, etc.

By further way of non-limiting example, in one embodiment, the optical wavelength of signal TS1 corresponds to a visible RED color of light such as between 600-760 nm. However, note that the wavelength of optical energy and signal TS1 can be any suitable value.

During exposure of the bio-media 125 to the signal TS1, a certain portion of the incident optical signal TS1 is reflected off of the bio-media 125 back to sensor hardware 261. Sensor hardware 261 produces signal S1 (such as an analog signal, digital signal, etc.), whose magnitude is proportional to an amount of the reflected optical signal, RS1, received by sensor hardware 261.

Note that as the respective subject under test 108 induces movement of the body part to which the monitor resource 120 is affixed, the portion of the incident signal TS1 that is reflected back to the sensor hardware 261 varies due to corresponding variations in the bio-media 125 being monitored. In other words, movement of the appendage of the subject under test 108 to which the monitor resource 120 is affixed causes attributes of the bio-media 125 under test to change.

As previously discussed, the bio-media 125 under test can include or be venous blood. Moving the appendage in a downward direction (such as toward the ground) causes an increase in the amount (volume) of the venous blood in the bio-media 125 being monitored. Conversely, moving the appendage in an upward direction (such as toward the sky) causes a decrease in the amount of the venous blood in the bio-media 125 being monitored.

As further discussed herein, the variations in the amount (volume) of venous blood in the bio-media 125 (fluid such as flowing blood) being monitored causes the reflected optical signal RS1 to be a modulated signal (i.e., a signal whose amplitude varies over time in accordance with the motion). Presence of more venous blood (such as a higher volume of fluid such as blood flowing through or occupying veins) in the bio-media 125 due to subject-induced movement decreases an amount of optical energy reflected off the respective bio-media 125. Conversely, presence of less venous blood in the bio-media 125 (such as a lower volume of fluid such as blood flowing through or occupying veins) due to subject-induced movement increases amount of optical energy reflected off the respective bio-media 125.

In a similar manner as discussed above, transmitter device 252 transmits optical signal TS2 (such as at a second optical wavelength) at bio-media 125. By way of non-limiting example, in one embodiment, the optical wavelength of signal TS2 corresponds to infrared energy such as optical energy between 840-1000 nm. However, note that the wavelength of optical energy and signal TS2 can be any suitable value.

As previously discussed, bio-media 125 can include any of more of the following matter: blood, tissue, bone, etc. During exposure of the bio-media 125 to the signal TS2, a certain portion of the incident optical signal TS2 is reflected off of the bio-media 125 back to sensor hardware 262. Sensor hardware 262 produces signal S2, whose magnitude is proportional to an amount of the reflected optical signal RS2 received by sensor hardware 262.

Note again that as the respective subject under test 108 induces movement of the body part to which the monitor resource 120 is affixed, the portion of the incident signal TS2 that is reflected back to the sensor hardware 262 varies due to corresponding variations in the bio-media 125 being monitored. In other words, movement of the appendage of the subject under test 108 to which the monitor resource 120 is affixed causes attributes of the bio-media 125 under test to change, resulting in more or less optical energy being reflected off the respective bio-media 125.

More specifically, the bio-media 125 under test can be or include venous blood. Moving the appendage in a downward direction (such as toward the ground) causes an increase in the amount of the venous blood in the bio-media 125 being monitored. Conversely, moving the appendage in an upward direction (such as toward the sky) causes a decrease in the amount of the venous blood in the bio-media 125 being monitored.

As further discussed herein, the variations in the amount of venous blood in the bio-media 125 being monitored causes the reflected optical signal RS2 to be a modulated signal (i.e., a signal whose amplitude varies over time in accordance with the motion).

Yet as further shown, the signal processor resource 140 receives a respective signals S1 and S2 (output 105) outputted from respective sensor hardware 261 and 262.

As its name suggests, signal processor resource 140 processes the received signals S1 and S2 to generate respective biometric setting information 155 subsequently displayed on display screen 130.

Further note that the monitor resource 120 can be configured to include motion detector 270 if desired. In such an embodiment, the motion detector 270 (such as an accelerometer or other suitable device) monitors motion along one or more axes to produce signal, MS, indicative of a magnitude and direction of the motion associated with the monitor resource 120 and corresponding body part of the subject under test 108 to which the monitor resource 120 is attached. If available, the signal processor resource 140 (further shown and discussed with respect to FIG. 4) uses the motion signal MS to determine occurrence of the variations in signals S1 and S2 caused by respective motion.

However, note that as further discussed below, use of the motion detector 270 is optional. That is, the signal processor resource 140 can be configured to analyze the signals S1 and S2 (further shown and discussed with respect to FIG. 5) to determine when motion occurs without the use of a motion signal, MS.

Note that the prior example of exposing the bio-media 125 with optical energy and measuring reflected optical energy is shown by way of non-limiting example. In accordance with alternative embodiments, note that the transmitter devices 251 and 252 as well as sensor hardware 261 and 262 can be replaced with an alternative type of excitation and monitoring circuits.

For example, in one embodiment the transmitter device 251 can be a voltage source that applies a first voltage signal (such as at a first frequency) across two nodes of the bio-media 125 under test. The sensor hardware 261 can be a current monitor circuit that detects changes in current across the bio media 125 during motion of the respective appendage to which the monitor resource 120 is attached. The changes in current can be used to derive settings for bio parameters of interest.

In a similar manner, the transmitter device 252 can be modified in a similar manner to monitor the bio-media 125 under test. For example, transmitter device 252 can be a voltage source that applies a second voltage signal (such as at a second frequency) across two nodes of the bio-media 125 under test. The sensor hardware 262 can be a current monitor circuit that detects changes in current across the bio-media 125 during motion of the respective appendage to which the monitor resource 120 is attached.

In accordance with yet further embodiments, the transmitter device 251 can be a current source that applies a first current through the bio-media 125 under test. The sensor hardware 261 can be a voltage monitor circuit that detects changes in voltage across the bio media 125 during motion of the respective appendage to which the monitor resource 120 is attached. Transmitter device 252 and sensor hardware 262 can be a modified in a similar manner.

Accordingly, embodiments herein can include injecting current through the bio-media 125 under test and then measuring voltage across the bio-media 125. Additionally, embodiments herein can include exposing the bio-media 125 to a voltage and then measuring variations in current through the bio-media 125 to produce signals S1 and S2.

Figure 3:
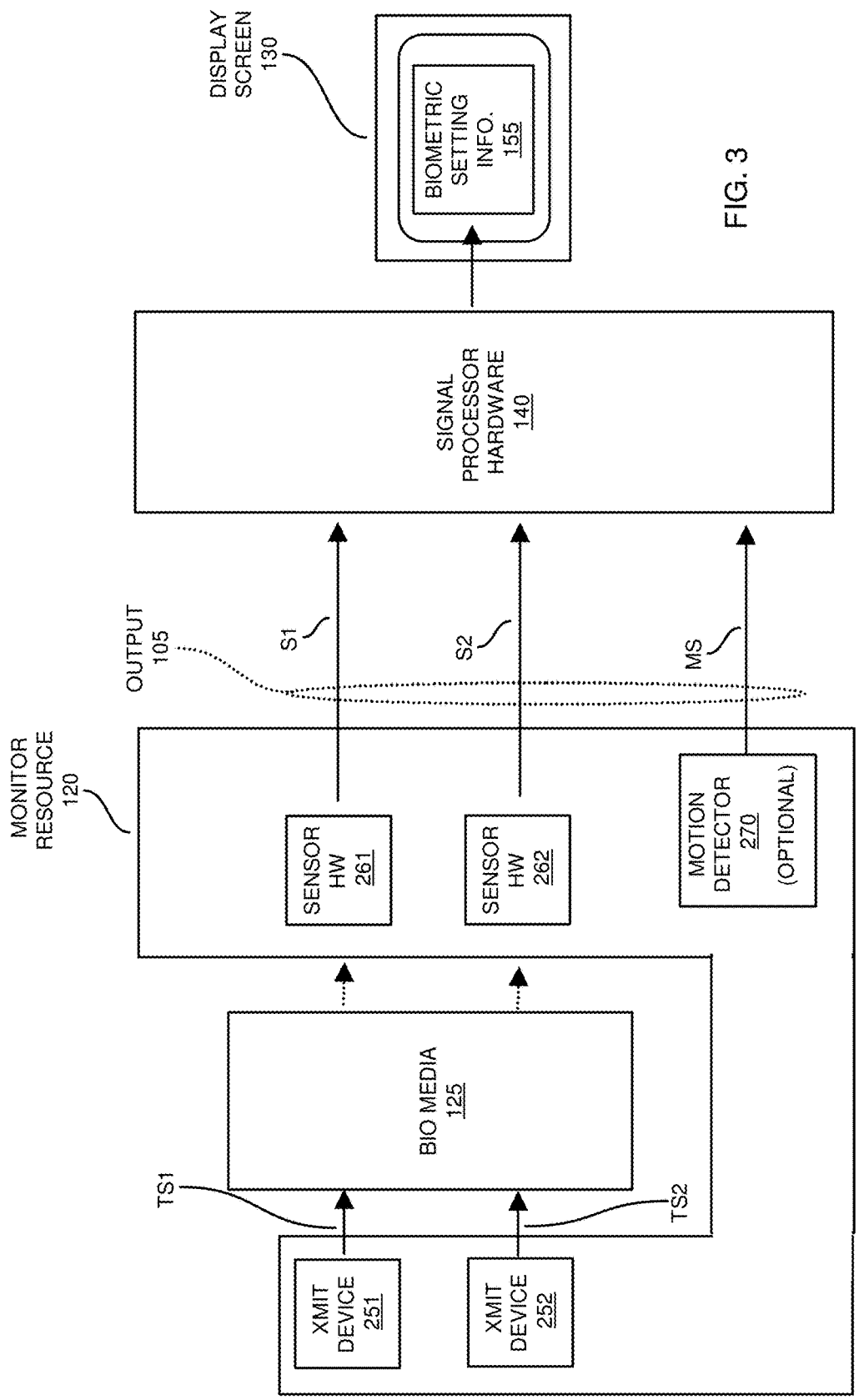
FIG. 3 is an example diagram illustrating use of monitor hardware to monitor bio-media, analysis of sensor-generated signals to produce display information, and display of corresponding monitor results according to embodiments herein.

FIG. 3 is an example diagram illustrating use of monitor hardware to monitor bio-media, analysis of sensor-generated signals to produce display information, and display of corresponding monitor results according to embodiments herein.

As an alternative to using reflected optical signals to produce signals S1 and S2, embodiments herein can include transmission of respective optical signals from transmitter devices 251 and 252 through the bio media 125.

In this example embodiment, instead of detecting a reflected portion of the optical signal generated by the transmitter device 251, the sensor hardware 261 detects an amount of the signal TS1 passing through the bio-media 125 to the sensor hardware 261. In such an instance, similar to the prior discussion with respect to FIG. 2, the sensor hardware 261 produces signal, S1, whose magnitude varies depending upon the amount of received optical energy transmitted through the bio-media 125 at the first optical wavelength.

Additionally, instead of detecting a reflected portion of the optical signal generated by the transmitter device 252, the sensor hardware 262 detects an amount of the signal TS2 passing through the bio-media 125 to the sensor hardware 262. In such an instance, the sensor hardware 262 produces signal S2 whose magnitude varies depending upon the amount of received optical energy transmitting through the bio-media 125 at the second optical wavelength.

In a similar manner as previously discussed, the signal processor resource 140 then uses the received signals S1 and S2 to generate biometric setting information 155 for display on display screen 130.

Figure 4:
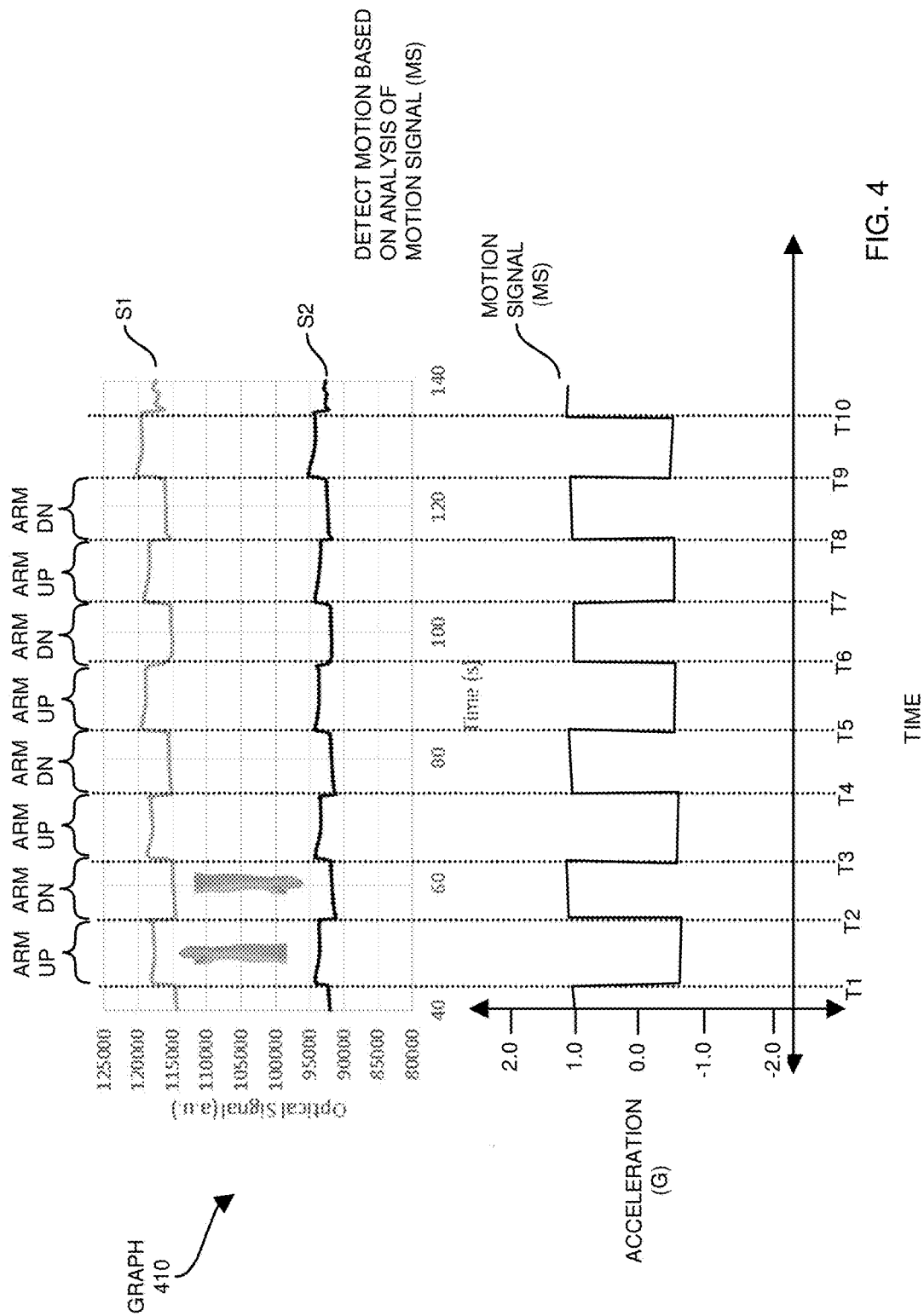
FIG. 4 is an example diagram illustrating use of a motion signal generated by a motion detector to identify attributes of motion according to embodiments herein.

FIG. 4 is an example diagram illustrating use of a motion signal generated by a motion detector to identify attributes of motion associated with the monitor resource and respective subject under test according to embodiments herein.

As shown in respective graph 410, motion signal MS indicates motion of the respective appendage to which the monitor resource 120 is attached. For example, motion signal MS indicates that at or around time T1, the respective subject under test 108 points her hand or arm up (which causes an increase in the amount of reflected optical energy sensed by the respective sensor devices 261 and 262); motion signal MS indicates that at or around time T2, the respective subject under test 108 points her hand or arm down (which causes a decrease in the amount of reflected optical energy sensed by the respective sensor devices 261 and 262); motion signal MS indicates that at or around time T3 that the respective subject under test 108 points her hand or arm up (which causes an increase in the amount of reflected optical energy sensed by the respective sensor devices 261 and 262); motion signal MS indicates that at or around time T4 that the respective subject under test 108 points her hand or arm down (which causes a decrease in the amount of reflected optical energy sensed by the respective sensor devices 261 and 262); and so on.

Accordingly, via the motion signal MS, the signal processor resource 140 is able to identify attributes of the motion associated with the monitor resource 120 and corresponding body part (bio-media 125) of the subject under test 108.

Alternatively, as further discussed below with respect to FIG. 5, the signal processor resource 140 can be configured to infer, from characteristics of the received modulated signals S1 and S2, when motion occurs.

Figure 5:
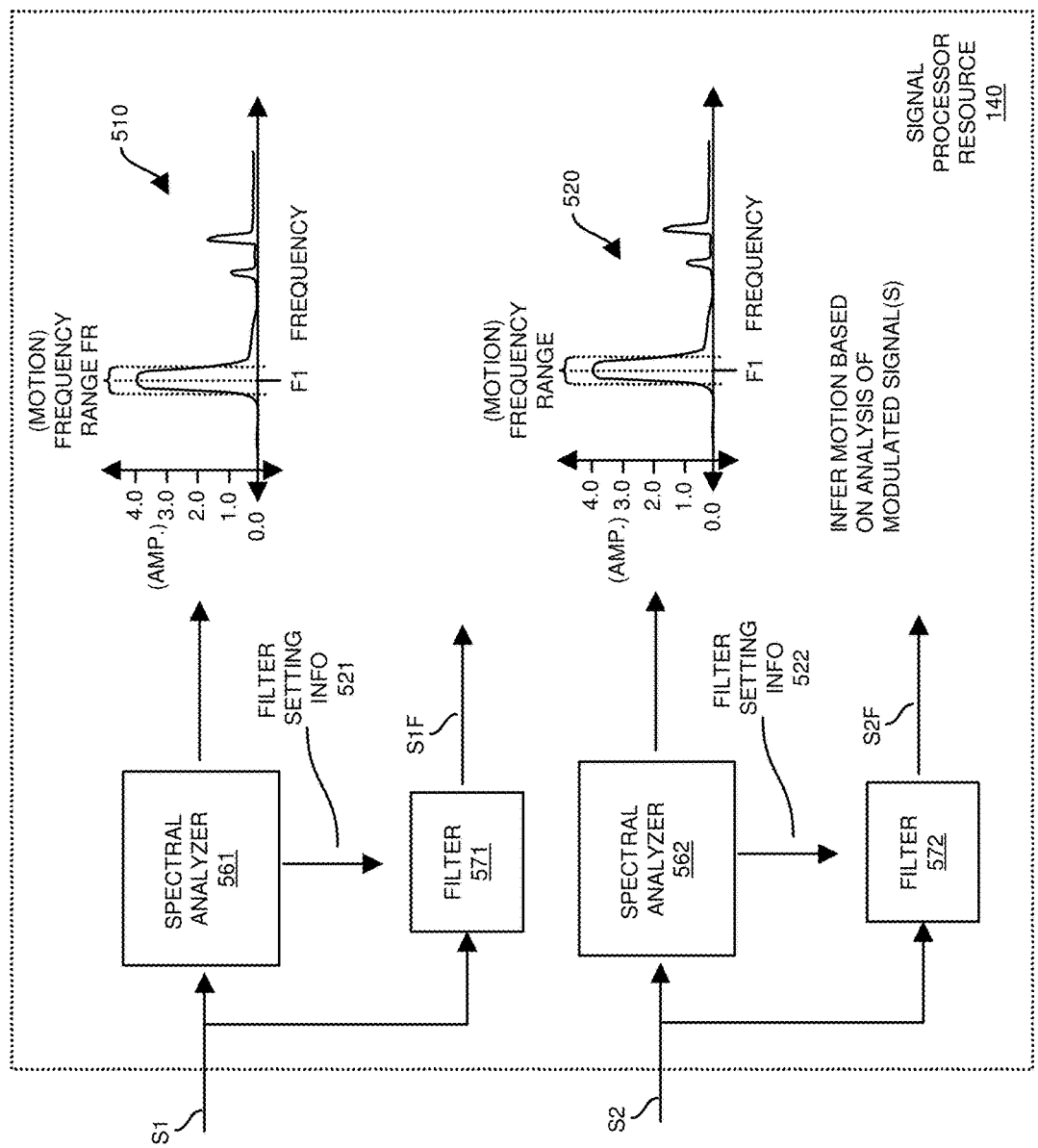
FIG. 5 is an example diagram illustrating spectral analysis of sensor-generated signals to infer and identify occurrence of motion according to embodiments herein.

More specifically, FIG. 5 is an example diagram illustrating spectral analysis of sensor-generated signals to identify motion according to embodiments herein.

In this example embodiment, the signal processor resource 140 includes spectral analyzer 561 to analyze received signal S1. Spectral analyzer 561 uses a Fast Fourier Transform algorithm or other suitable algorithm to generate information in graph 510 indicating the different frequencies and corresponding magnitudes of signal component associated with received signal S1. In this example embodiment, graph 510 indicates that one predominant frequency associated with signal S1 and corresponding motion occurs around frequency, F1. Frequency F1 and respective frequency range FR corresponds to the frequency of motion associated with monitor resource 121 and corresponding body part to which the monitor resource 120 is attached.

In furtherance of generating the setting for one or more biometric parameters of interest, the signal processor resource 140 generates filter setting information 521 to control settings of filter 571. In this example embodiment, the filter setting information 521 sets the filter 571 (such as a bandpass filter) to block frequencies outside of frequency range FR and pass frequencies of the input signal S1 that fall within the frequency range FR. Frequency components of signal S1 outside of the frequency range FR may include harmonics or other components that are not of interest. Accordingly, the output signal S1F (representing an AC portion of the original signal S1) is a filtered version of received signal S1.

In a similar manner, the signal processor resource 140 can include spectral analyzer 562. In such an instance, the spectral analyzer 562 analyzes frequency components of the received signal S2 and generates filter setting information 522 to configure filter 572. In a manner as previously discussed, the filter setting information 522 sets the filter 572 (such as a bandpass filter) to block frequencies outside of frequency range FR and pass frequencies of the input signal S2 that fall within the frequency range, FR. Frequency components of signal S2 outside of the frequency range FR may include harmonics or other components that are not of interest. Accordingly, the output signal S2F (representing an AC portion of the original signal S2) is a filtered version of the received signal S2.

As further discussed in the following figures, the signal processor resource 140 uses the processing as discussed in FIG. 4 and/or FIG. 5 to identify different portions (AC portions, DC portions) of the signals S1 and S2 in which to produce biometric data (i.e., biometric setting information 155) associated with the monitored bio-media 125.

Figure 6:
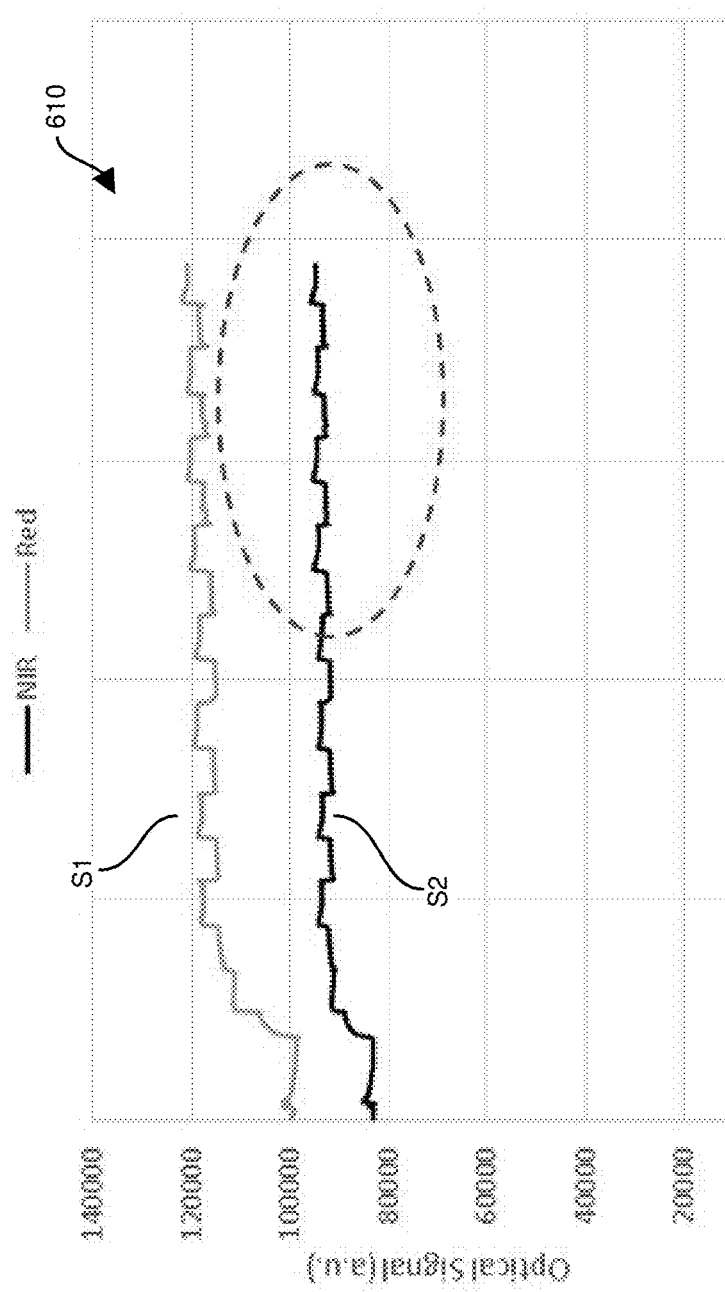
FIG. 6 is an example diagram illustrating sensor-generated signals according to embodiments herein.

FIG. 6 is an example diagram illustrating sensor-generated signals according to embodiments herein.

As shown in graph 610, signals S1 and S2 vary over time due to motion of the appendage to which the monitor resource 120 is attached.

Figure 7:
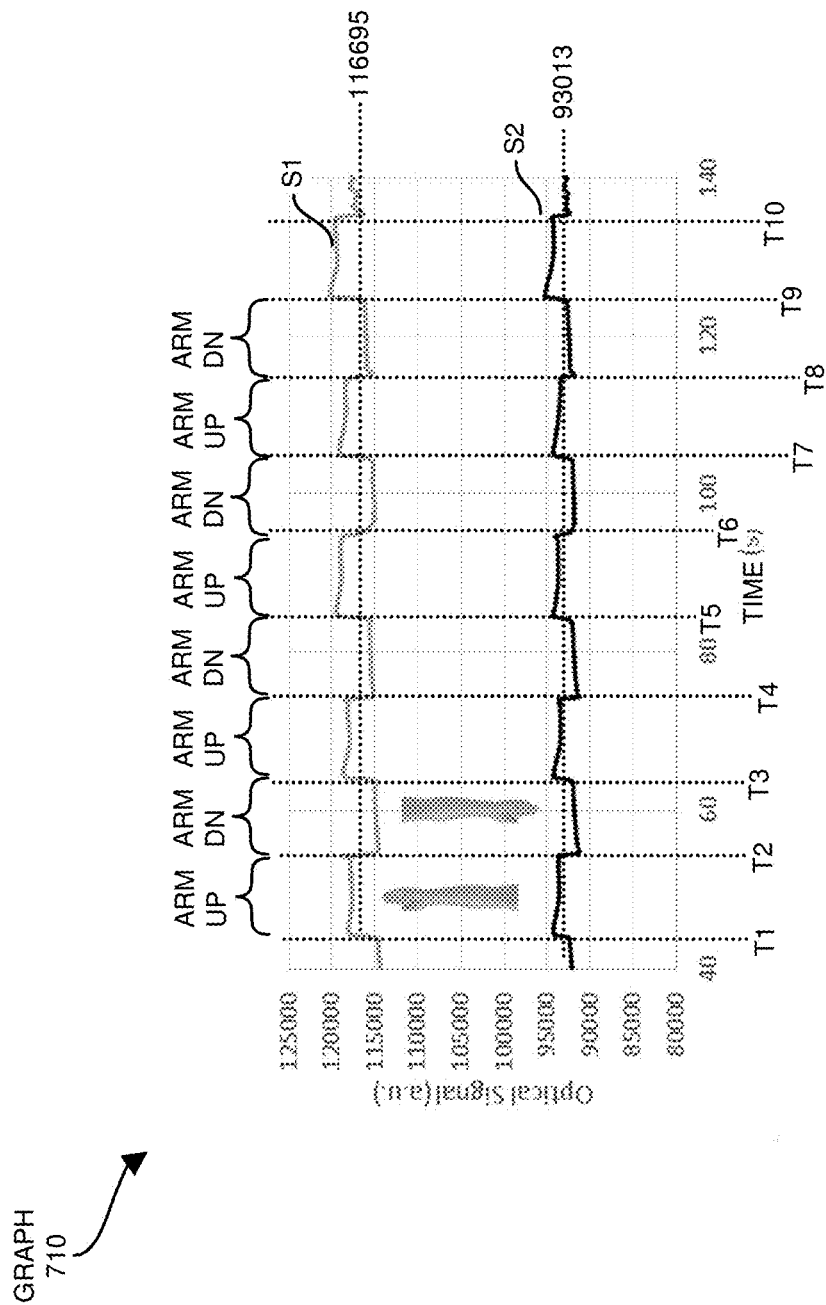
FIG. 7 is an example diagram illustrating how motion of monitored bio-media causes signal modulation according to embodiments herein.

FIG. 7 is an example more detailed diagram illustrating how motion of monitored bio-media causes signal modulation according to embodiments herein.

As previously discussed, the sensor hardware generates signal S1 based on detecting reflected signal RS1 (see also FIG. 2); sensor hardware 262 generates signal S2 based on detecting reflected signal RS2 (see also FIG. 2).

Each of generated signals S1 and S2 in this example is modulated (such as in a step-like manner) based on motion-induced variations in the bio-media 125 monitored by the monitor resource 120. In other words, the motion of the subject under test 108 causes attributes of the bio-media 125 to change over time; the change in the attributes of the bio-media 125 causes different amounts of optical energy to be reflected back to the sensor hardware 261 and 262.

As shown in respective graph 710, the subject under test 108 or caregiver initiates movement of the body part to which the monitor resource 120 is affixed. In one embodiment, the subject under test 108 causes movement of the body part in a manner as specified by instructions provided by any suitable entity (such as a caregiver, automated software such as an application on a phone device providing instructions reminding the subject under test 108 what to do or when it is time to take a measurement, etc.). For example, the entity can notify the subject under test 108 to move her arm up and down at a desired rate. In one embodiment, the desired rate is substantially slower than a normal heart rate of the human such as less than 50 movements per minute or greater than 150 movements per minute to avoid confusing the heartbeat of the user as being a motion of the user.

Note that the motion also can be normal daily activity of a respective subject such as walking or climbing up or down stairs, jogging, walking, etc. The motion from any of these self-induced activities results in modulation of the bio-media 125 under test as described herein.

Further in this example, at or around time T1, the respective subject under test 108 causes motion of pointing her hand or arm up (which causes an increase in the amount of reflected optical energy sensed by the respective sensor devices 261 in 262); at or around time T2, the respective subject under test 108 causes motion of pointing her hand or arm down (which causes a decrease in the amount of reflected optical energy sensed by the respective sensor devices 261 in 262); at or around time T3, the respective subject under test 108 causes motion of pointing her hand or arm up (which causes an increase in the amount of reflected optical energy sensed by the respective sensor devices 261 in 262); at or around time T4, the respective subject under test 108 causes motion of pointing her hand or arm down (which causes a decrease in the amount of reflected optical energy sensed by the respective sensor devices 261 in 262); and so on.

In one embodiment, as previously discussed, the bio-media 125 under test includes bio matter such as venous blood, bone, tissue, etc. Generally, the reflected signals RS1 and RS2 include multiple components of reflected optical energy from different bio matter under test. For example, bone matter in the bio-media 125 reflects a first amount of the incident optical energy from signal TS1; tissue matter in the bio-media 125 reflects a second amount of the incident optical energy from signal TS1; venous blood in the bio-media 125 reflects a third amount of the incident optical energy from signal TS1; and so on.

By way of further non-limiting example, variations in the magnitudes (AC portions) of the signals S1 and S2 are primarily due to motion-induced variations in the amount of venous blood monitored by the sensor hardware 261 and 262. More specifically, the motion of the subject under test 108 in the down position increases the amount of venous blood monitored by the monitor resource 120, decreasing the overall amount of reflected incident optical energy from signal TS1; the motion of the subject under test 108 in the up position decreases the amount of venous blood monitored by the monitor resource 120, increasing the overall amount of reflected incident optical energy from signal TS1. The amount of reflection attributable to other bio matter (such as non-blood bio matter) in the bio-media 125 monitored by the monitor resource 120 is generally constant regardless of the motion.

Thus, the variations in the output 105 are useful for analyzing one or more different types of biometric parameters.

As further discussed below, the DC and AC portions of the signals S1 and S2 can be used generate settings for one or more biometric parameters of interest.

Figure 8:
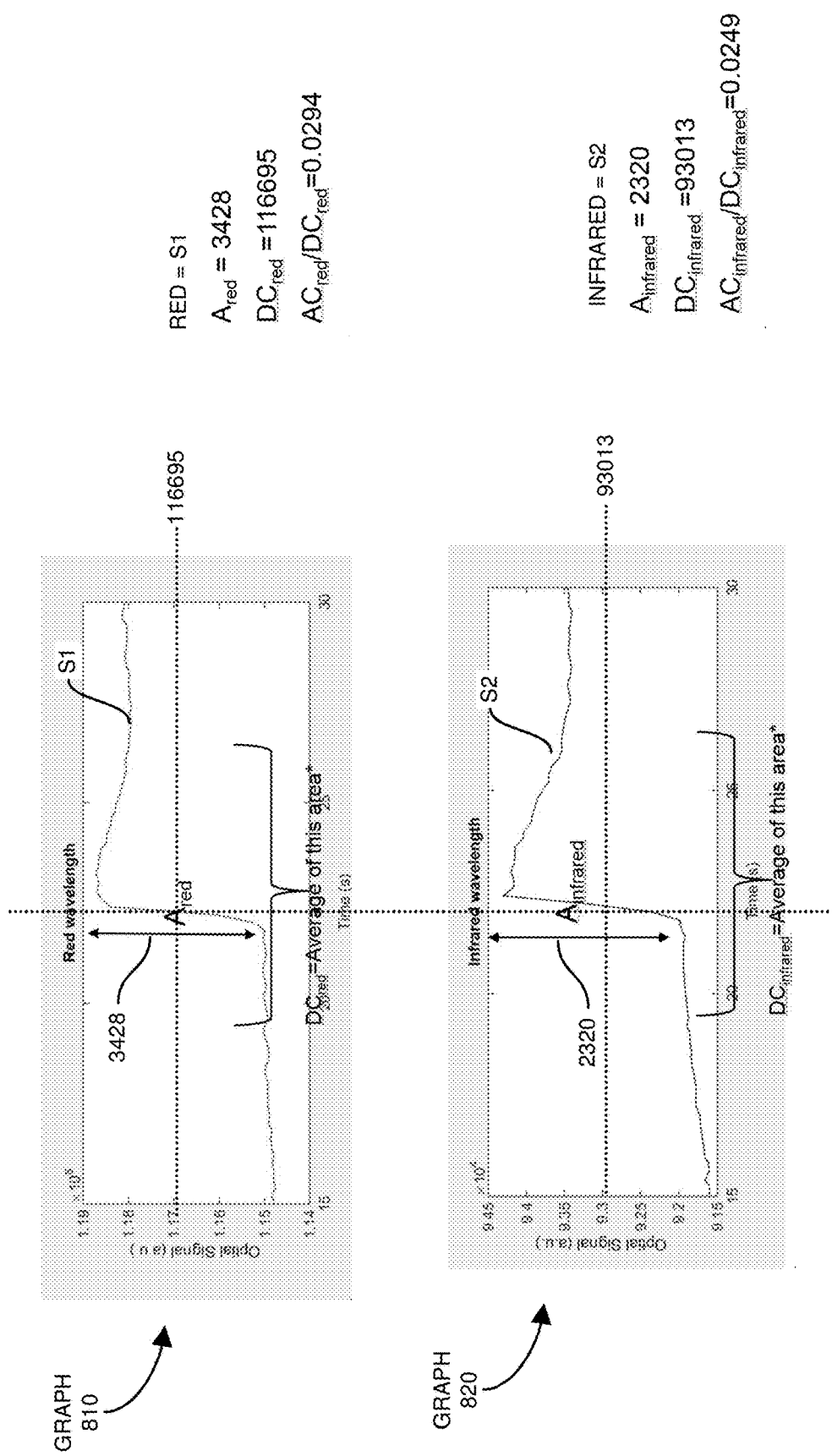
FIG. 8 is an example diagram illustrating analysis of sensor-generated signals to identify respective AC and DC components according to embodiments herein.

FIG. 8 is an example diagram illustrating analysis and use of sensor-generated signals to produce settings for one or more biometric parameters according to embodiments herein.

In this example, the bio-media 125 under test includes venous blood. To measure a biometric parameter such as venous blood oxygen saturation (SvO2) of the bio-media 125, the signal processor resource 140 implements the following equations to produce a setting for SvO2:

$$\text{Ratio \#1} = AC_{S1}/DC_{S1}, \qquad \text{equation (1)}$$

where $AC_{S1}$ represents a magnitude of frequency components (AC component) of signal S1 that fall in the frequency range, FR, (or a transition between levels in signal S1 that happens at time T1 or T2 or T3 where the motion was identified) and $DC_{S1}$ represents an overall magnitude (DC component) of signal S1 at or around sample time such as T3.

$$\text{Ratio \#2} = AC_{S2}/DC_{S2}, \qquad \text{equation (2)}$$

where $AC_{S2}$ represents a magnitude of frequency components (AC components) of signal S2 that fall in the range, FR, (or a transition between levels in signal S2 that happens at time T1 or T2 or T3 where the motion was identified) and $DC_{S2}$ represents an overall magnitude (DC components) of signal S2 at or around a sample time such as T3.

The signal processor resource 140 uses the following equation to produce a setting for SvO2 as follows:

$$\text{Final Ratio} = [\text{Ratio \#1}/\text{Ratio \#2}]*CF, \qquad \text{equation (3)}$$

where CF=calibration factor associated with system 100.

In the present example, based on analysis of signals S1 and S2 as shown in graphs 810 and 820 in FIG. 8, the signal processor resource 140 measures the amplitude of the AC portion of signal S1 around time T3 to be 3428 units (i.e., $AC_{S1}$=3428 units). The signal processor resource 140 measures the average of the magnitude of the DC portion of signal S1 as shown such as in a time range around time T3 (see also FIG. 7) to be 116,695 units. (i.e., $DC_{S1}$=116,695 units). In such an instance:

$$\text{Ratio \#1} = AC_{S1}/DC_{S1}, = 3428/116{,}695 = 0.0294. \qquad \text{equation (4)}$$

Additionally, the signal processor resource 140 measures the amplitude of the AC portion of signal S2 around time T3 to be 2320 units (i.e., $AC_{S2}$=2,320 units). The signal processor resource 140 measures the average of the amplitude of the DC portion of signal S2 as shown such as in a time range around T3 (see also FIG. 7) to be 93,013 units. (i.e., $DC_{S2}$=93,013 units). In such an instance:

$$\text{Ratio \#2} = AC_{S2}/DC_{S2} = 2{,}320/93{,}013 = 0.0249. \quad \text{equation (5)}$$

Using the following equation, assuming that CF is equal to one, the signal processor resource 140 produces a value for the Final Ratio to be:

$$\text{Final Ratio} = [\text{Ratio \#1}/\text{Ratio \#2}]*CF = [0.0294/0.0249]*1 = 1.1807 \quad \text{equation (6)}$$

Using the following equation, assuming that CF is equal to one, the signal processor resource 140 produces a value for SvO2 using a calibration curve that can vary between different implementations:

$$SvO2(T3) = 110 - [25*\text{Final Ratio}] = 110 - [25*1.1807] = 80.5\% \quad \text{eqn. (7)}$$

As previously discussed, the signal processor resource 140 also can be configured to generate a value for additional biometric parameters. For example, the signal processor resource 140 can be configured to generate a value for vein stiffness associated with a venous matter in a vicinity of the bio-media 125 monitored by the monitor resource 120.

As a specific example, the signal processor resource 140 can be configured to use the following equation to generate vein stiffness:

$$V\text{stiffness} = K*[\text{Ratio \#1}/F] = K*AC_{S1}/DC_{S1}*[1/F], \quad \text{equation (8)}$$

where K=calibration factor of system 100,
where $AC_{S1}$ represents a magnitude of frequency components (AC components) of signal S1 that fall in the range FR and $DC_{S1}$ represents an overall magnitude (DC components) of signal S1,
where F=a respective force of moving the body part of the subject under test 108, a value of which is known from signal MS as measured by motion detector 270.

For stiffer (less flexible) veins, the amount of modulation of respective signals S1 and S2 is lower. For more flexible (less stiff) veins, the amount of modulation of respective signals S1 and S2 is higher. Note that when F and/or K are not available, the same system can be used uncalibrated to track trends of venous stiffness over time by monitoring the trends in Ratio #1 only. A higher ratio for the same force/motion indicates a lower stiffness value.

In accordance with further embodiments, the signal processor resource 140 further can be configured to generate modulation index values:

$$MI_{S1} = AC_{S1}/DC_{S1}, \text{ and} \quad \text{equation (9)}$$

$$MI_{S2} = AC_{S2}/DC_{S2}. \quad \text{equation (10)}$$

Accordingly, the signal processor resource 140 can be configured to use the output 105 from the monitor resource 120 to generate biometric setting information 155 for multiple biometric parameters such as SvO2, Vstiffness, $MI_{S1}$, $MI_{S2}$, etc., for display on display screen 130

Figure 9:
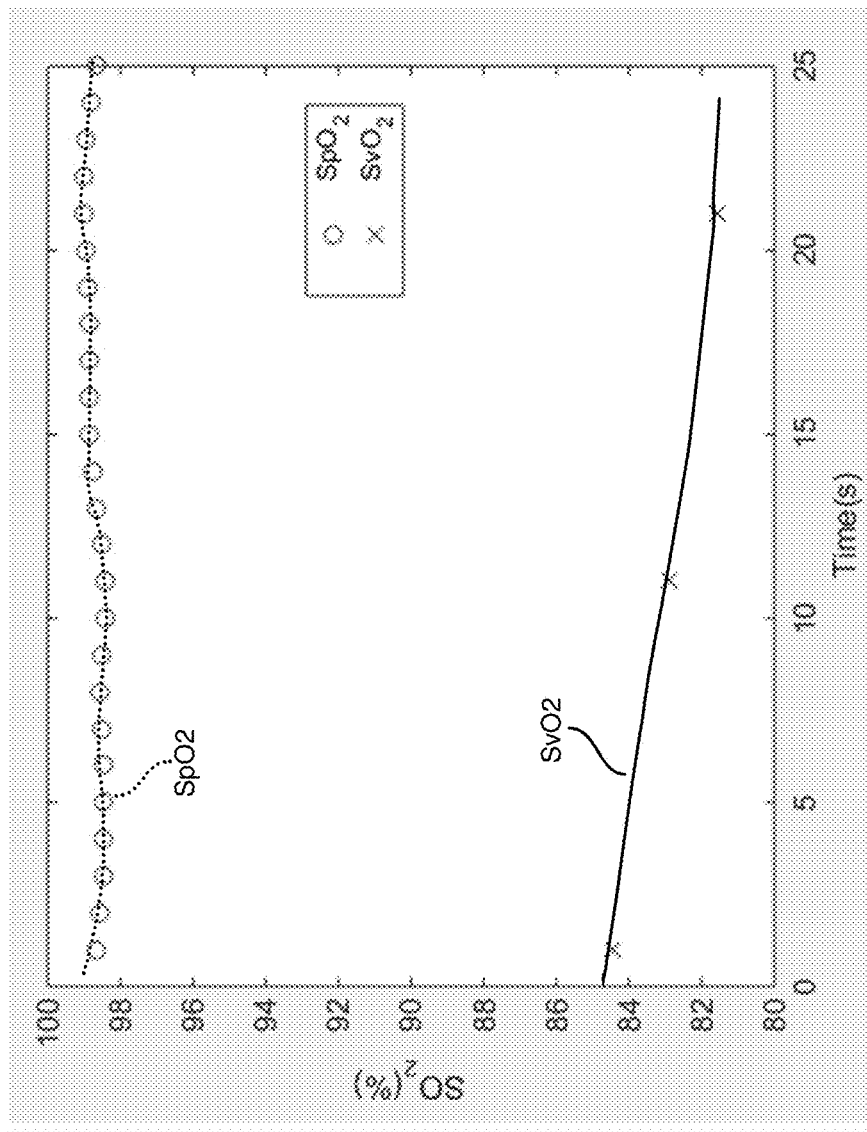
FIG. 9 is an example diagram illustrating display of peripheral oxygen saturation with respect to venous oxygen saturation according to embodiments herein.

FIG. 9 is an example diagram illustrating display of peripheral oxygen saturation with respect to venous oxygen saturation according to embodiments herein.

As previously discussed, the signal processor resource 140 monitors any of one or more biometric parameters over time. Graph 910 illustrates an example of displaying SpO2 versus SvO2 over time, such as on display screen 130 as previously discussed.

In a similar manner as previously discussed for signals S1 and S2 at time T3, the signal processor resource 140 can be configured to generate a respective value for biometric parameter SvO2 (for venous blood) over each of multiple sample times such as T4, T5, T6, etc., using a similar analysis as previously discussed for display of such data on display screen 130. Biometric parameter SpO2 represents a measure of oxygenation associated with arterial blood using any suitable apparatus.

Note further that, if desired, settings obtained at multiple different sample times for a given biometric parameter of interest can be averaged to produce a respective setting value for the biometric parameter on display screen 130.

Figure 14:
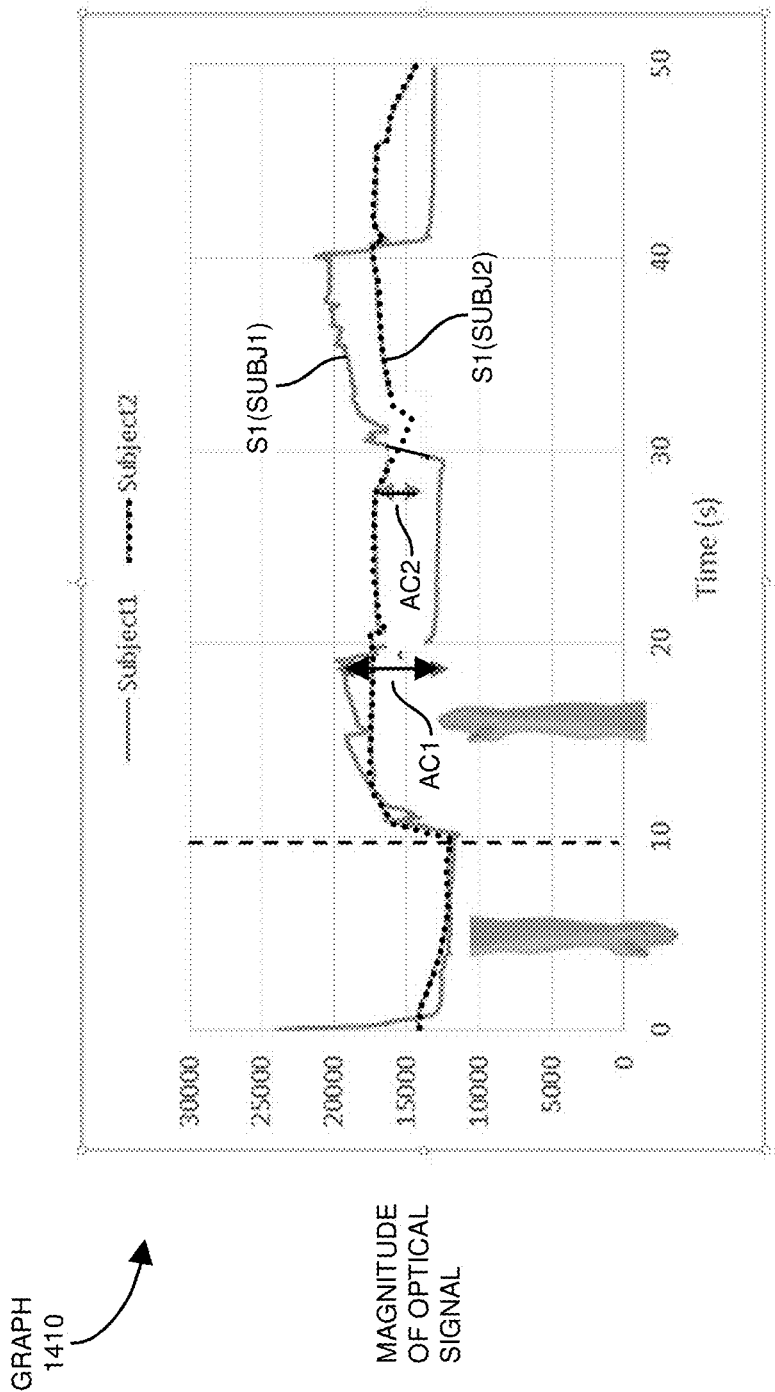
FIG. 14 is an example diagram illustrating sensor-generated signals to measure vessel stiffness according to embodiments herein.

FIG. 14 is an example diagram illustrating sensor-generated signals according to embodiments herein.

Graph 1410 indicates signal variations caused by motion associated with two different subjects, namely, subject #1 (such as a 23-year-old person) and subject #2 (such as a 30-year-old person). Note that vessel stiffness typically increases with age; accordingly, in this example, veins of subject #2 are stiffer than those of subject #1.

As further discussed, signal processor resource 140 uses the output 105 (S1 and S2) generated from the monitor resource 120 to identify a degree of blood vessel stiffness. Each of the subjects uses a different monitor system 100 (FIG. 1) (or same monitor system at different times) to measure corresponding file media 125 under test.

Assume that a first monitor resource 120-1 monitors subject #1 and produces signal S1(SUBJ1) such as a signal representing reflected RED light; assume that a second monitor resource 120-2 monitors subject #2 and produces signal S1(SUBJ2) such as a signal representing reflected light.

As shown in graph 1410, each of the subjects moves their respective monitored arm every 10 seconds. For example, at time=0 seconds, each of the subjects lowers their arm; at time=10 seconds, each of the subjects raises their arm; at time=20 seconds, each of the subjects lowers their arm; at time=30 seconds, each of the subjects raises their arm; and so on. In a manner as previously discussed, this motion causes a volume of venous blood in a monitored bio-media to vary for the given subject under test.

In such an instance, for the red wavelength, a first signal processor resource 140 associated with a first monitor resource 120 analyzes the signal S1(SUBJ1) and detects that AC1(RED)=8000 and that DC1(RED)=15000 as shown. For subject #1, the signal processor resource 140-1 uses these values (for RED) to produce a ratio of AC1/DC1=8000/15000=0.53 or 53%.

Additionally, for the red wavelength, a second signal processor resource 140 associated with a second monitor resource 120 analyzes the signal S1(SUBJ2) and detects that, for subject #2, AC1(RED)=3000 and that DC1(RED)=15000. Thus, for subject #2, the signal processor resource 140-2 uses these values (for RED the wavelength) to produce a ratio of AC1/DC1=3000/15000=0.20 or 20%.

In general, the ratio of AC/DC is smaller for subject #2 for the red wavelength, indicating that subject #2 has stiffer veins than subject #1. To obtain an absolute measure of stiffness, calibration coefficients can be used.

Figure 15:
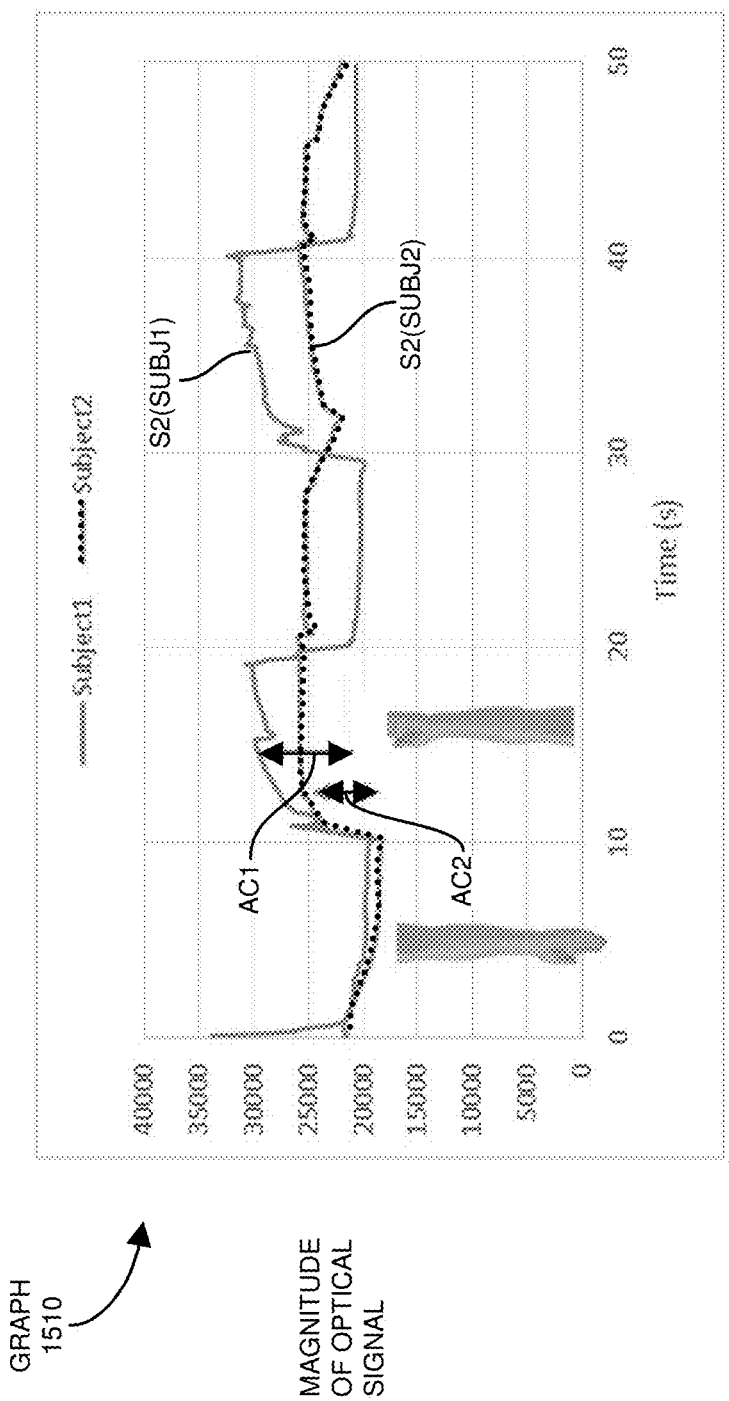
FIG. 15 is an example diagram illustrating sensor-generated signals to measure vessel stiffness according to embodiments herein.

FIG. 15 is an example diagram illustrating sensor-generated signals according to embodiments herein.

Graph 1510 indicates signal variations caused by motion associated with same subjects as above, namely, subject #1 (such as a 23-year-old person) and subject #2 (such as a 30-year-old person).

As previously mentioned, vessel stiffness typically increases with age; accordingly, in this example, vessels of subject #2 are stiffer than those of subject #1.

As further discussed, a first signal processor resource 140 uses the output 105 generated from a monitor resource 120 to identify a degree of blood vessel stiffness. As previously discussed, each of the subjects uses a different monitor resource 120 to measure corresponding bio-media 125 under test.

Assume that a first monitor resource 120-1 monitors subject #1 and produces signal S2(SUBJ1); assume that a second monitor resource 120-2 monitors subject #2 and produces signal S2(SUBJ2).

Note that signal S1(SUBJ1) in graph 1410 and S2(SUBJ1) in graph 1510 are collected at the same time via respective resources such as first sensor hardware 261 and 262. Note that signal S1(SUBJ2) in graph 1410 and S2(SUBJ2) in graph 1510 are collected at the same time via respective resources such as second sensor hardware 261 and 262.

As shown in graph 1510, in a similar manner as discussed above, each of the subjects moves their arm every 10 seconds. For example, at time=0 seconds, each of the subjects lowers their arm; at time=10 seconds, each of the subjects raises their arm; at time=20 seconds, each of the subjects lowers their arm; at time=30 seconds, each of the subjects raises their arm; and so on.

In such an instance, for the infrared wavelength, first signal processor resource 140 associated with first monitor resource 120 analyzes the signal S2(SUBJ1) and detects that AC1(INFRARED)=8000 and that DC1(INFRARED)=15000 as shown. For subject #1, the signal processor resource 140 uses these values (for INFRARED) to produce a ratio of AC1/DC1=10000/23000=0.43 or 43%.

Additionally, for the infrared wavelength, second signal processor resource 140 associated with second monitor resource 120 analyzes the signal S2(SUBJ2) and detects that AC1(INFRARED)=3000 and that DC1(INFRARED)=22500. For subject #2, the second signal processor resource 140 uses these values (for INFRARED) to produce a ratio of AC1/DC1=3000/22500=0.13 or 13%.

As mentioned, in general, the ratio of AC/DC is smaller for subject #2 for both red and infrared wavelengths, indicating that subject #2 has stiffer veins than subject #1. In other words, assuming that movement is substantially similar between both subject #1 and subject #2, the vessels in subject #1 (because they are more flexible) fill with more blood upon movement than do the vessels of subject #2. To obtain an absolute measure of stiffness, appropriate calibration coefficients for the measurement system can be used.

In accordance with yet further embodiments, note further that for venous stiffness, in addition to, or as an alternative to measuring the AC/DC ratio (modulation rate) as discussed above, one can use the rate of decay or increase in the signal in response to a mechanical motion to accomplish similar results. For example, instead of using AC/DC ratio as described herein, which is the amount of change (AC) normalized by DC, one can use the amount of change per unit time (dAC/dt) normalized by DC as well.

Figure 10:
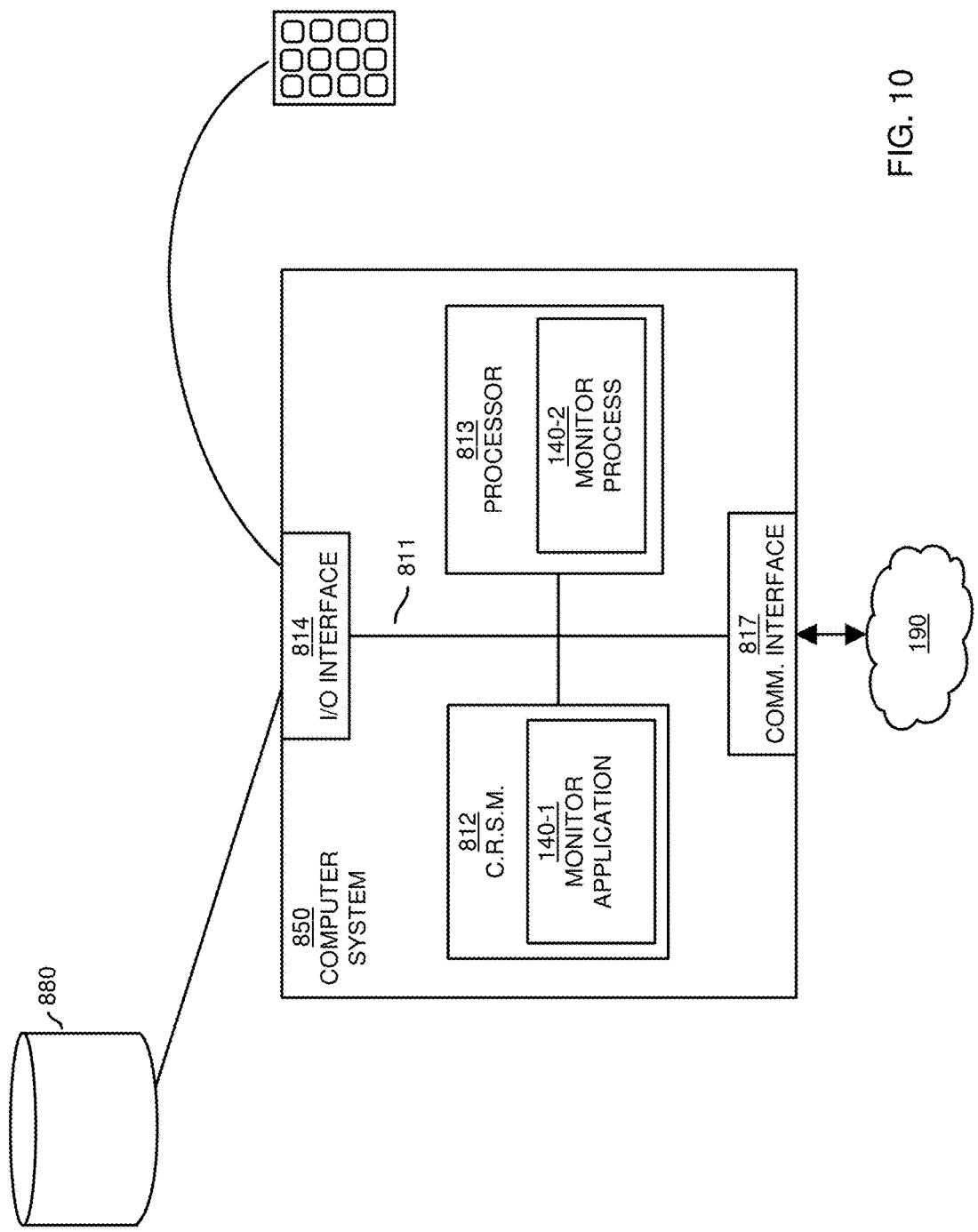
FIG. 10 is an example diagram illustrating a computer architecture in which to execute one or more applications according to embodiments herein.

FIG. 10 is an example block diagram of a computer apparatus for implementing any of the operations as discussed herein according to embodiments herein.

Any of the resources (e.g., monitor resource 120, signal processor resource 140, etc.) can be configured to include a processor and executable instructions to carry out the different operations as discussed herein.

As shown, computer system 850 of the present example includes an interconnect 811 that couples computer readable storage media 812 such as a non-transitory type of media (i.e., any type of hardware storage medium) in which digital information can be stored and retrieved, a processor 813 (computer processor hardware), I/O interface 814, etc.

Computer readable storage medium 812 can be or include any hardware storage device such as memory, optical storage, hard drive, floppy disk, etc. In one embodiment, the computer readable storage medium 812 stores instructions and/or data.

As shown, computer readable storage media 812 can be encoded with monitor application 140-1 (e.g., including instructions) to carry out any of the operations as discussed herein associated with the monitor resource 120, signal processor resource 140, etc.

During operation of one embodiment, processor 813 accesses computer readable storage media 812 via the use of interconnect 811 in order to launch, run, execute, interpret or otherwise perform the instructions in monitor application 140-1 stored on computer readable storage medium 812. Execution of the monitor application 140-1 produces monitor process 140-2 to carry out any of the operations and/or processes as discussed herein.

Those skilled in the art will understand that the computer system 850 can include other processes and/or software and hardware components, such as an operating apparatus that controls allocation and use of hardware resources to monitor application 140-1.

In accordance with different embodiments, note that computer apparatus may be or included in any of various types of devices, including, but not limited to, a mobile computer, a personal computer apparatus, a wireless device, base station, phone device, desktop computer, laptop, notebook, netbook computer, mainframe computer apparatus, handheld computer, workstation, network computer, application server, storage device, a consumer electronics device such as a camera, camcorder, set top box, mobile device, video game console, handheld video game device, a peripheral device such as a switch, modem, router, set-top box, content management device, handheld remote control device, any type of computing or electronic device, etc.

The computer system 850 may reside at any location or can be included in any suitable one or more resources in a network environment to implement functionality as discussed herein.

Functionality supported by the different resources will now be discussed via flowcharts in FIGS. 11-13. Note that the steps in the flowcharts below can be executed in any suitable order.

Figure 11:
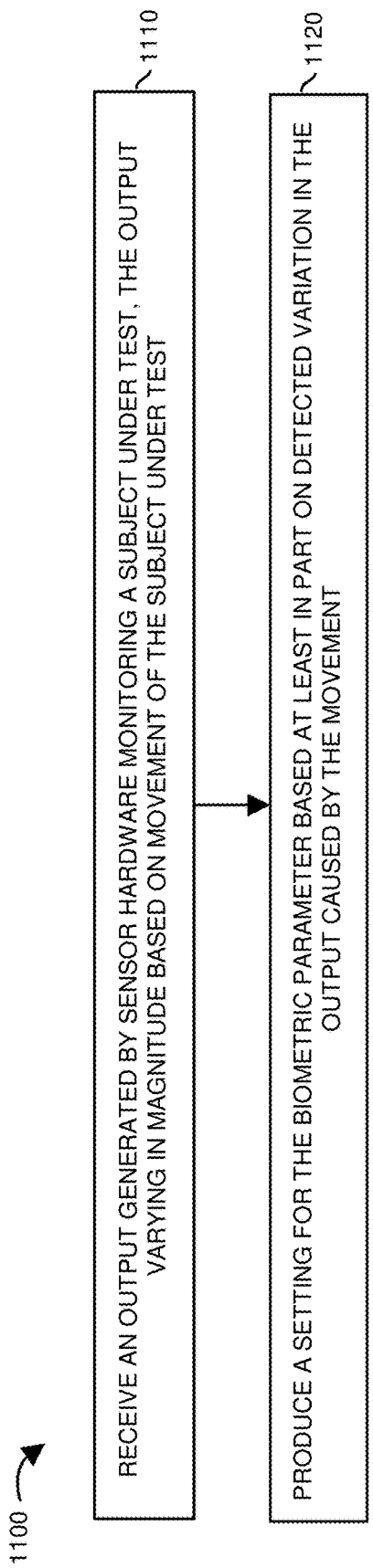
FIGS. 11-13 are example diagrams illustrating various methods according to embodiments herein.

FIG. 11 is a flowchart 1100 illustrating an example method according to embodiments. Note that there will be some overlap with respect to concepts as discussed above.

In processing operation 1110, the signal processor resource 140 receives an output 105 (one or more signals) generated by sensor hardware 261 and 262 monitoring bio-media 125 of a subject under test 108. The output 105 varies in magnitude based on movement of the subject under test 108.

Figure 12:
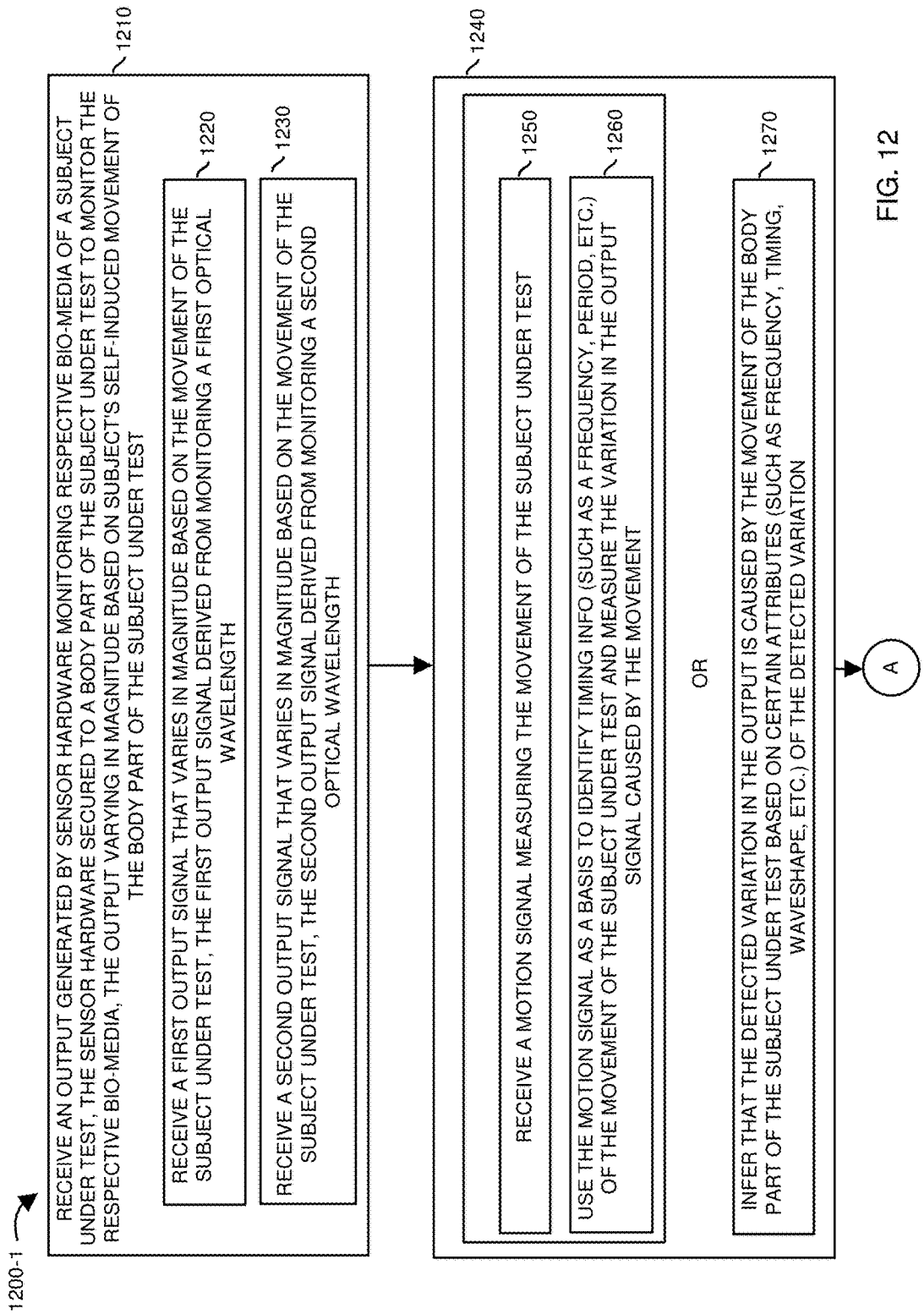

In processing operation 1120, the signal processor resource 140 produces a setting for the biometric parameter based at least in part on detected variation in the output caused by the subject's movement FIG. 12 is a flowchart 1200 illustrating an example method according to embodiments. Note that there will be some overlap with respect to concepts as discussed above.

In processing operation 1210 of flowchart 1200-1, the signal processor resource 140 (such as monitor application 140-1) receives output 105 generated by sensor hardware 261 and 262 monitoring respective bio-media 125 of the subject under test 108. In one embodiment, as previously discussed, the monitor resource 120, including sensor hardware 261 and 262, is secured to a body part of the subject under test 108 to monitor respective bio-media 125. The output 105 (such as one or more monitor signals) varies in magnitude based on subject-induced movement of the body part of the subject under test 108.

In sub-processing operation 1220, the signal processor resource 140 receives a first output signal S1 that varies in magnitude based on the movement of the subject under test 108. In one embodiment, the sensor hardware 261 produces the first output signal S1 based on monitoring a first optical wavelength of light reflecting off of and/or passing through bio-media 125.

In sub-processing operation 1230, the signal processor resource 140 receives a second output signal S2 that varies in magnitude based on the movement of the subject under test 108. In one embodiment, the sensor hardware 262 produces the second output signal S2 based on monitoring a second optical wavelength of light reflecting off of or passing through bio-media 125.

In processing operation 1240, the signal processor resource 140 analyzes the received output 105 to determine an amount of modulation caused by motion. For example, in one embodiment, in sub-processing operation 1250, the signal processor resource 140 receives a motion signal, MS, measuring the movement of the subject under test 108. In one embodiment, in sub-processing operation 1260, the signal processor resource 140 uses the motion signal, MS, as a basis to identify timing attributes (such as a frequency, period, etc.) of the movement of the subject under test 108 and subsequently measure the variation in the output signal 105 caused by the detected movement.

As an alternative to receiving and using the motion signal, MS, or other suitable metric to identify attributes of moment associated with subject under test 108 and corresponding bio-media 125 under test, in accordance with sub-processing operation 1270, the signal processor resource can be configured to analyze modulation associated with the received signals S1 and S2 and infer that detected variations (modulated portion of signals) in the output 105 (signals S1 and S2) are caused by the movement of a respective body part of the subject under test 108. For example, as previously discussed, in one embodiment, the signal processor resource 140 performs a analysis of the signals S1 and S2 to determine certain attributes (such as frequency, timing, wave shape, etc.) associated with modulation of the received modulated signals S1 and S2 generated by the sensor hardware 261 and 262.

Figure 13:
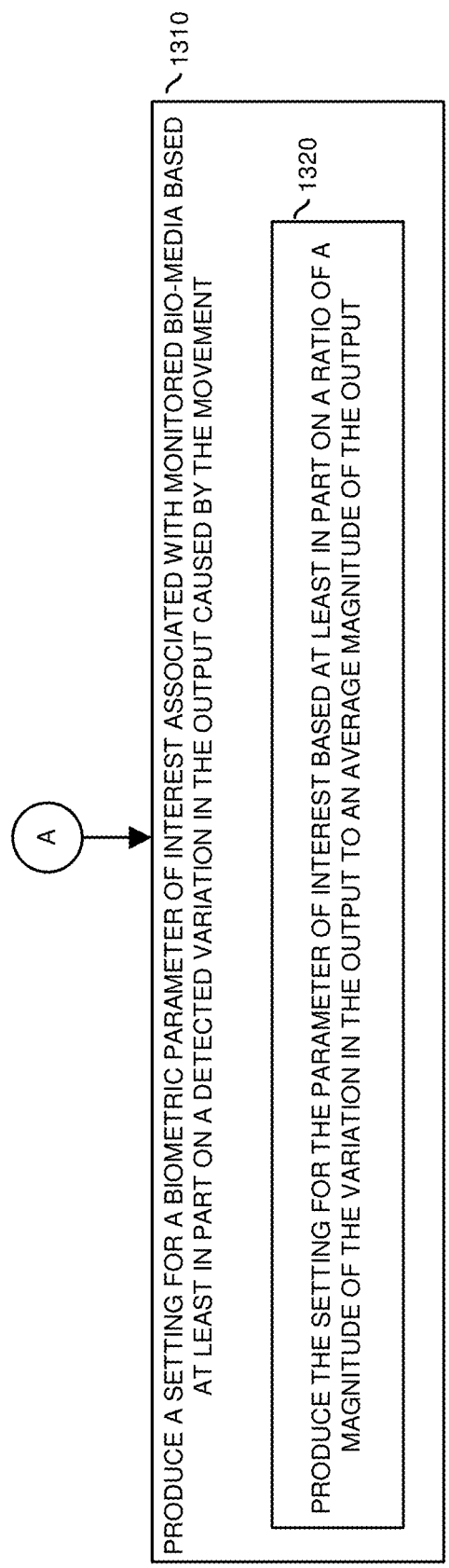

In processing operation 1310 of FIG. 13, the signal processor resource 140 produces a setting for a biometric parameter of interest associated with monitored bio-media 125 based at least in part on a detected variation in the output 105 (one or more signals S1 and S2) caused by the movement.

In sub-processing operation 1320, the signal processor resource 140 produces the setting for the parameter of interest based at least in part on a ratio of a magnitude of the variation (such as AC portion) in an output signal to an average magnitude of the output signal.

Note again that techniques herein are well suited to support monitor bio-media such as blood and produce settings for one or more bio parameters of interest. However, it should be noted that embodiments herein are not limited to use in such applications and that the techniques discussed herein are well suited for other applications as well.

Based on the description set forth herein, numerous specific details have been set forth to provide a thorough understanding of claimed subject matter. However, it will be understood by those skilled in the art that claimed subject matter may be practiced without these specific details. In other instances, methods, apparatuses, apparatus s, etc., that would be known by one of ordinary skill have not been described in detail so as not to obscure claimed subject matter. Some portions of the detailed description have been presented in terms of algorithms or symbolic representations of operations on data bits or binary digital signals stored within a computing apparatus memory, such as a computer memory. These algorithmic descriptions or representations are examples of techniques used by those of ordinary skill in the data processing arts to convey the substance of their work to others skilled in the art. An algorithm as described herein, and generally, is considered to be a self-consistent sequence of operations or similar processing leading to a desired result. In this context, operations or processing involve physical manipulation of physical quantities. Typically, although not necessarily, such quantities may take the form of electrical or magnetic signals capable of being stored, transferred, combined, compared or otherwise manipulated. It has been convenient at times, principally for reasons of common usage, to refer to such signals as bits, data, values, elements, symbols, characters, terms, numbers, numerals or the like. It should be understood, however, that all of these and similar terms are to be associated with appropriate physical quantities and are merely convenient labels. Unless specifically stated otherwise, as apparent from the following discussion, it is appreciated that throughout this specification discussions utilizing terms such as "processing," "computing," "calculating," "determining" or the like refer to actions or processes of a computing platform, such as a computer or a similar electronic computing device, that manipulates or transforms data represented as physical electronic or magnetic quantities within memories, registers, or other information storage devices, transmission devices, or display devices of the computing platform.

While this invention has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of embodiments of the present application is not intended to be limiting. Rather, any limitations to the invention are presented in the following claims.

We claim:

1. An apparatus to measure a biometric parameter of a user while filtering the user's voluntary body movement, the apparatus comprising:
   sensor hardware configured to monitor the user and produce an output signal and a motion signal, the output signal from the sensor hardware varying based on the movement; and
   a signal processor configured to:
      identify a frequency range associated with the movement based on the motion signal;

produce a filter to pass portions of the output signal in the frequency range,
pass the output signal through the filter to measure a variation in the output signal caused by the movement, and
produce biometric data for the biometric parameter based at least in part on the variation in the output signal caused by the movement.

2. The apparatus as in claim 1, wherein the sensor hardware produces the output signal based on monitoring bio-media of the user, wherein attributes of the bio-media vary due to the movement, and the output signal varies due to movement-induced variations in the bio-media.

3. The apparatus as in claim 1 further comprising:
a motion detector for detecting the movement and producing the motion signal, wherein the signal processor uses the motion signal to identify attributes of the movement and to measure the variation in the output signal caused by the movement.

4. The apparatus as in claim 3, wherein the signal processor is configured to produce the biometric data based at least in part on a ratio of a magnitude of the variation in the output signal to an average magnitude of the output signal.

5. The apparatus as in claim 1, wherein the output signal includes a portion of an optical signal reflected off bio-media of the user monitored by the sensor hardware; and
wherein the biometric data as produced by the signal processor is a level of oxygen saturation associated with the bio-media monitored by the sensor hardware.

6. The apparatus as in claim 1, wherein the sensor hardware is configured to be secured to a body part of the user; and
wherein the movement of the user is movement of the body part, which causes the variation in the output signal.

7. The apparatus as in claim 6, further comprising instructions provided to the user, wherein the instructions direct the user to move the body part in a manner as specified by the instructions.

8. The apparatus as in claim 1, wherein the output signal includes a first output signal from the sensor hardware, the first output signal varying in magnitude based on the movement; and
wherein the output signal from the sensor hardware includes a second output signal, the second output signal varying in magnitude based on the movement.

9. The apparatus as in claim 8, wherein the signal processor is further configured to produce a first ratio value, the first ratio value representing a ratio of the magnitude of the variation in the first output signal to an average magnitude of the first output signal; and
wherein the signal processor is further configured to produce a second ratio value, the second ratio value representing a ratio of the magnitude of the variation in the second output signal to an average magnitude of the second output signal.

10. The apparatus as in claim 9, wherein the signal processor produces the biometric data based at least in part on dividing the first ratio value by the second ratio value.

11. The apparatus as in claim 1, wherein the sensor hardware, disposed at an external location of a body of the user, non-invasively monitors venous blood flow to produce the output signal; and
wherein the biometric data produced by the signal processor is oxygen saturation in the venous blood.

12. A method to measure a biometric parameter of a user, the method comprising:
receiving an output and a motion signal generated by sensor hardware monitoring the user, the output varying in magnitude based on movement of the user;
producing a filter to pass portions of the output in a frequency range associated with the movement based on the motion signal;
passing the output through the filter to measure a variation in the output caused by the movement; and
producing biometric data for the biometric parameter based at least in part on the variation in the output caused by the movement.

13. The method as in claim 12, wherein the movement is person-induced movement of a body part of the user.

14. The method as in claim 13, wherein the sensor hardware monitors fluid bio-media of the user, and a volume of the fluid bio-media monitored by the sensor hardware varies due to the movement.

15. The method as in claim 12 further comprising:
receiving the motion signal measuring the movement; and
using the motion signal to identify frequency attributes of the movement and to measure the variation in the output signal caused by the movement.

16. The method as in claim 12, wherein producing the biometric data for the biometric parameter includes:
inferring that the variation in the output is caused by a movement of a body part of the user based at least in part on a frequency of the variation.

17. The method as in claim 12, wherein the sensor hardware is configured to be secured to a body part of the user; and
wherein the movement of the body part causes the variation in the output from the sensor hardware.

18. Non-transitory computer-readable storage media having instructions stored thereon for measuring a biometric parameter of a user, the instructions, when executed by computer processor hardware, cause the computer processor hardware to:
receive an output and a motion signal generated by sensor hardware monitoring the user, the output signal varying based at least in part on movement of the user; and
produce a filter to pass portions of the output in a frequency range associated with the movement based on the motion signal;
pass the output through the filter to measure a variation in the output caused by the movement; and
produce biometric data for a biometric parameter based at least in part on detected variations in the output caused by the movement.

19. The computer-readable storage media of claim 18, wherein the sensor hardware monitors fluid bio-media of the user, and a volume of the fluid bio-media monitored by the sensor hardware varies due to the movement.

20. The computer-readable storage media of claim 18, wherein the instructions, when executed by computer processor hardware, further cause the computer processor to:
use the motion signal to identify frequency attributes of the movement and to measure the variation in the output caused by the movement.

* * * * *